(12) United States Patent
Buxbaum et al.

(10) Patent No.: US 8,691,762 B2
(45) Date of Patent: Apr. 8, 2014

(54) METHODS AND ASSAYS FOR TREATING SUBJECTS WITH SHANK3 DELETION, MUTATION OR REDUCED EXPRESSION

(75) Inventors: Joseph Buxbaum, New York, NY (US); Takeshi Sakurai, New York, NY (US); Ozlem Gunal, New York, NY (US)

(73) Assignee: Mount Sinai School of Medicine, New York, NY (US)

( * ) Notice: Subject to any disclaimer, the term of this patent is extended or adjusted under 35 U.S.C. 154(b) by 0 days.

(21) Appl. No.: 13/425,633

(22) Filed: Mar. 21, 2012

(65) Prior Publication Data

US 2012/0216302 A1    Aug. 23, 2012

Related U.S. Application Data

(63) Continuation-in-part of application No. PCT/US2011/000860, filed on May 16, 2011.

(60) Provisional application No. 61/395,775, filed on May 17, 2010.

(51) Int. Cl.
*A61K 38/30* (2006.01)

(52) U.S. Cl.
USPC .......................................................... 514/8.6

(58) Field of Classification Search
None
See application file for complete search history.

(56) References Cited

U.S. PATENT DOCUMENTS

| | | | |
|---|---|---|---|
| 8,263,611 B2 * | 9/2012 | Grinter et al. | 514/299 |
| 2009/0099077 A1 | 4/2009 | Sur et al. | |
| 2009/0297573 A1 | 12/2009 | Sur et al. | |
| 2011/0166029 A1 * | 7/2011 | Margulies et al. | 506/7 |

FOREIGN PATENT DOCUMENTS

WO    2006128133 A1    11/2006
WO    2009/143622 A1    12/2009

OTHER PUBLICATIONS

Pasini A et al., entitled "Dose-dependent effect of risperidone treatment in a case of 22q13.3 deletion syndrome," Brain Dev. May 2010;32(5):425-7.
Altar C A et al., entitled "Insulin IGF-1, and muscarinic agonists modulate schizophrenia-associated genes in human neuroblastoma cells," Biol Psychiatry, Dec. 15, 2008;64(12):1077-87.
Bozdagi O et al., entitled "Haploinsufficiency of the autism-associated Shank3 gene leads to deficits in synaptic function, social interaction, and social communication," Molecular Autism, Dec. 17, 2010, 1:15.
Durand C M et al., entitled "Mutations in the gene encoding the synaptic scaffolding protein Shank3 are associated with autism spectrum disorders," Nature Genetics, vol. 39, No. 1, Jan. 2007, 25-27.
Moessner R et al., entitled "Contribution of Shank3 Mutations to Autism Spectrum Disorder," The American Journal of Human Genetics, vol. 81, Dec. 2007, 1289-1297.
Qin J et al., entitled "Associated study of Shank3 gene polymorphisms with autism in Chinese Han Population," BMC Medical Genetics 2009, 10:61, 1-6.
Trejo J et al., entitled "Central actions of liver-derived insulin-like growth factor I underlying its pro-cognitive effects," Molecular Psychiatry, 2007, 12, 1118-1128.

* cited by examiner

*Primary Examiner* — Marianne P Allen
(74) *Attorney, Agent, or Firm* — Amster, Rothstein & Ebenstein LLP

(57) ABSTRACT

Methods and assays are disclosed for treating subjects with 22q13 deletion syndrome or SHANK3 deletion or duplication, mutation or reduced expression, where the methods comprise administering to the subject insulin-like growth factor 1 (IGF-1), IGF-1-derived peptide or analog, growth hormone, an AMPAkine, a compound that directly or indirectly enhances glutamate neurotransmission, including by inhibiting inhibitory (most typically GABA) transmission, or an agent that activates the growth hormone receptor or the insulin-like growth factor 1 (IGF-1) receptor, or a downstream signaling pathway thereof.

1 Claim, 12 Drawing Sheets

A

B

A

B

SEQUENCE LISTING

<160> NUMBER OF SEQ ID NOS: 3

<210> SEQ ID NO 1
<211> LENGTH: 217
<212> TYPE: PRT
<213> ORGANISM: Homo sapiens -continued

<400> SEQUENCE: 1

```
Met Ala Thr Gly Ser Arg Thr Ser Leu Leu Ala Phe Gly Leu Leu
 1               5                  10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```

<210> SEQ ID NO 2
<211> LENGTH: 191
<212> TYPE: PRT
<213> ORGANISM: Homo sapiens

<400> SEQUENCE: 2

```
Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140
```

```
Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 3
<211> LENGTH: 70
<212> TYPE: PRT
<213> ORGANISM: Homo sapiens

<400> SEQUENCE: 3

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65              70
```

METHODS AND ASSAYS FOR TREATING SUBJECTS WITH SHANK3 DELETION, MUTATION OR REDUCED EXPRESSION

CROSS-REFERENCE TO RELATED APPLICATIONS

This application is a continuation-in-part of and claims priority of PCT International Patent Application No. PCT/US2011/000860, filed May 16, 2011, which designates the United States of America, and claims the benefit of U.S. Provisional Patent Application No. 61/395,775, filed May 17, 2010, the contents of which are herein incorporated by reference in their entirety.

STATEMENT OF GOVERNMENT SUPPORT

This invention was made with government support under grant number MH093725 awarded by the National Institute of Mental Health. The government has certain rights in the invention.

FIELD OF THE INVENTION

The present invention relates generally to methods, and assays for compounds, for treating subjects with 22q13 deletion syndrome or SHANK3 deletion, duplication, mutation or reduced expression.

BACKGROUND OF THE INVENTION

Throughout this application various publications are referred to in short form. Full citations for these references may be found at the end of the specification. The disclosures of these publications are hereby incorporated by reference in their entirety into the subject application to more fully describe the art to which the subject invention pertains.

22q13 deletion syndrome. Chromosome 22q13 deletion syndrome, also known as Phelan-McDermid Syndrome, was first described in case reports in the early 90s, culminating in a review of the 24 published cases and 37 additional cases by Phelan et al. (2001). The studies conclusively demonstrated that individuals identified with 22q13 deletion syndrome had global developmental delay and absent or severely delayed expressive speech. Furthermore, the overwhelming majority of cases had hypotonia (97%) with normal or accelerated growth (95%). The developmental delay is associated with mental retardation typically in the mild-to-moderate range. Other, less universal, features included large hands (>75%), dysplastic toenails (>75%), and decreased perspiration. Behavior characteristics include mouthing or chewing non-food items (>75%), decreased perception of pain (>75%), and autism or autistic-like traits. Approximately 75% of individuals with a 22q13 deletion syndrome diagnosis have either a 22 q terminal deletion (i.e., a chromosome break in 22q with loss of the segment distal to the break), or an interstitial deletion (i.e., two breaks within the same chromosome arm and loss of the intervening segment). The remaining 25% of individuals diagnosed with 22q13.3 deletion syndrome had deletions resulting from an unbalanced translocation or other structural rearrangement, including ring 22.

Hypotonia, global developmental delay and speech deficits together represent some of the most consistent findings, each in >95% of all patients. The hypotonia in newborns with the syndrome can be associated with weak cry, poor head control, and feeding difficulties leading to failure to thrive. In terms of developmental delay, in addition to the mental retardation noted above, there is also evidence for a delay to major milestones, such that, for example, the average age for rolling over is approximately eight months, for crawling approximately 16 months, and for walking approximately three years. Poor muscle tone, lack of balance, and decreased upper body strength contribute to the delay in walking and ultimately, gait is often broad-based and unsteady. Finally, while infants with the syndrome typically babble at the appropriate age and children may acquire a limited vocabulary, by approximately age four years many children have significant deficits in the ability to speak. With intensive therapy, the individuals with the syndrome may have some speech and increase their vocabularies. It is interesting to note that receptive communication skills are more advanced than expressive language skills as demonstrated by the ability of affected children to follow simple commands, demonstrate humor, and express emotions.

Role of SHANK3 in 2203 deletion syndrome. Three lines of evidence implicated a single gene, SHANK3 (for SH3 and multiple ankyrin repeat domains 3, also referred to as proline-rich synapse associated protein 2/PROSAP2), in 22q13 deletion syndrome. First, careful analysis of the extent of the deletion in independent cases indicated a small critical region encompassing SHANK3. Thus, an analysis of 33 cases with various forms of monosomy of chromosome 22 (include ring 22, which as noted above is phenotypical similarly to the deletion syndrome) showed that the 12 with simple deletions had deletions of variable in size (from 160 kb to 9 Mb), with a minimal critical region responsible for the phenotype including SHANK3, ACR, and RABL2B (Luciani et al., 2003). Similarly, an analysis of 56 patients with the syndrome again demonstrated a very variable size of the deletion (130 kb to 9 Mb) with deletion of SHANK3 found in all cases explicitly tested, including the smallest deletion, with the minimal region encompassing the same three genes (Wilson et al., 2003). Remarkably, the severity of the behavioral phenotype was not correlated with the size of the deletion, indicating that haploinsufficiency of just one or more of these three genes was primarily responsible for the phenotype. Higher resolution studies have now identified patients with even smaller deletions, which exclude ACR and RABL2B from the minimal region, leaving only SHANK3 as the causal gene for the deletion syndrome (Bonaglia et al., 2011).

The second line of evidence was the demonstration of a recurrent breakpoint in SHANK3 in some cases with 22q13 deletion syndrome. The first report of a translocation with a breakpoint in SHANK3 associated with 22q13 deletion syndrome already made the point that disruption of SHANK3 likely underlied the disorder (Bonaglia et al., 2001). This group went on the identify two additional cases (Bonaglia et al., 2006), both with a breakpoint within the same 15-bp repeat unit in the SHANK3 gene (which overlapped with another SHANK3 breakpoint described by Wong et al., 1997). The presence of recurrent disruptions in SHANK3 led to the conclusion that disruption of this one gene is sufficient for the generation of 22q13 deletion syndrome.

Role of SHANK3 in autism spectrum disorders (ASD). Mutations directly in SHANK3 also resulting in the main features of 22q13 deletion syndrome represent the final line of evidence. Thus, while it has become increasingly recognized that 22q13 deletion syndrome can present with ASD and in fact 22q13 deletions are commonly associated with ASD in literature surveys (Vorstman et al., 2006), three recent studies explored the separate question as to whether SHANK3 disruption and mutations can be found in cohorts with apparently idiopathic ASD. In the first such study (Durand et al., 2007), SHANK3 was analyzed by both FISH and by direct sequencing in as many as 227 individuals with ASD. Three variants were identified. First, an individual with a de novo deletion of SHANK3 was identified; this individual had autism (narrowly defined), absent language, and moderate mental retardation. Second, a paternally inherited translocation was identified that resulted in a deletion of the 22q13 region (including SHANK3) in a girl with autism and severe language delay, and a duplication of the same region in her brother with Asperger syndrome. Finally, Durand et al. (2007) identified two brothers with autism, severely impaired speech, and severe mental retardation, which carried a single-base insertion in SHANK3. The insertion, which was maternal in origin (likely due to germline mosaicism in the mother), resulted in a frameshift at the COOH-terminal of the protein that disrupts domains involved in Homer and cortactin binding and the sterile alpha motif (SAM) domain involved in assembly of the SHANK3 platform. Overexpression of the mutant form in cultured hippocampal neurons did not lead to synaptic localization of the heterologous protein, in contrast to the wild-type SHANK3 protein.

In a follow up to Durand et al. (2007), Moessner et al. (2007), examined both sequence and SHANK3 gene dosage in 400 individuals with ASD. Two deletions were identified, as well as 1 de novo mutation. Furthermore, an additional deletion was identified in two siblings from an additional collection. The mutation, found in a girl with autism, results in a Q321R change in the ankyrin repeat domain at the NH2 terminal of SHANK3.

In a third study, Gauthier et al. (2009) sequenced SHANK3 in 427 ASD subjects and identified a de novo deletion at an intronic donor splice site and a missense variant transmitted from an epileptic father.

A de novo splice site variant of the SHANK3 gene has also been reported in a patient with mental retardation and severe language delay (Hamdan et al., 2011). In addition, Shank3 mutant mice display autistic-like behaviours (Bozdagi et al. 2010; Bangash et al., 2011; Peca et al., 2011; Wang et al., 2011).

Remarkably, SHANK3 mutations can also result in schizophrenia, including atypical schizophrenia associated with mental retardation and/or early onset as recently shown by Gauthier et al. (2010).

Altogether, these studies strongly support a role for disruptions of SHANK3 in developmental delay and ASD. Clearly, haploinsufficiency of SHANK3, caused either by a chromosomal abnormality or a mutation, can result in a profound phenotype. Furthermore, even overexpression of SHANK3 can result in developmental disorders (considering, for example, the case with Asperger syndrome and three copies of the SHANK3 locus reported in Durand et al., 2007 or the case with three copies and ADHD reported in Moessner et al., 2007). Recent, very large scale studies in clinical samples demonstrate that ca. 0.3% of patients with intellectual disability referred to for chromosome microarray have a SHANK3 deletion or duplication (Cooper et al., 2011). With the advent of clinical sequencing, point mutations in SHANK3 are also being identified in the clinical setting and evidence from research studies indicates a similar rate (ca. 0.3%) making SHANK3 deletions and mutations one of the more common monogenic causes of developmental delay syndromes, intellectual disability and ASD.

Function of SHANK proteins in the structure of the synapse. The post-synaptic density (PSD) is an electron-dense structure underlying the postsynaptic membrane in glutamatergic synapses in the central nervous system (Okabe, 2007). The PSD is most commonly found on dendritic spines of pyramidal neurons of the neocortex and hippocampus and Purkinje cells of the cerebellum, as well as on dendritic shafts at sites of contact with interneurons in the neocortex and hippocampus, as well as motoneurons in the spinal cord. As such the PSD represents a critical organelle for glutamatergic transmission. It has been shown that the SHANK proteins (including SHANK3) are a major part of the PSD. Multiple analytical approaches, including the characterization of antibodies directed against PSD preparations, two-hybrid screens, gel electrophoresis and mass spectrometry and other modern proteomic approaches have placed the SHANK proteins in the PSD (reviewed in Boeckers, 2006 and Okabe, 2007). Moreover, recent quantitative methods have estimated that there are about 300 individual SHANK molecules in a single postsynaptic site, representing something in the order of 5% of the total protein molecules and total protein mass in the site (Sugiyama et al., 2005). As it has been postulated that SHANK proteins may nucleate the protein framework for the PSD, a recent study examined the ability of the sterile alpha motif (SAM) of SHANK3 to form polymers by self-association (Baron et al., 2006). As with other SAM domains (Qiao and Bowie, 2005), the SAM domain of SHANK3 was able to self-associate, giving rise to large sheets of parallel fibers. These studies support the hypothesis that sheets of the SHANK proteins can form the scaffold or platform onto which the PSD is constructed. Such a role for the SHANK proteins has led to them being called "master scaffolding proteins" of the PSD.

The SHANK protein interactome. With the SHANK proteins (including SHANK3) forming a molecular platform onto which the PSD protein complex can be constructed, other proteins and protein complexes of the PSD can associate with the SHANK platform. Of the various protein complexes associated with glutamatergic synapses, there is good evidence that the NMDA receptor complex (NRC), the metabotropic glutamate receptor complex (mGC), and the AMPA receptor complex (ARC) associate with the SHANK platform (see Boeckers, 2006).

The NRC (Husi et al., 2000), analyzed after isolation by affinity purification, includes receptors, scaffolding proteins, signaling proteins, and cytoskeletal proteins. Amongst the scaffolding proteins identified in the NRC are the SHANK proteins, and it is thought that NMDA receptors are anchored to the SHANK platform through the mediation of PSD-95 and SAPAP/GKAP (see Boeckers, 2006). Thus, NMDA receptors are tethered to the postsynaptic membrane by interaction with PDZ domains of PSD-95, while the guanylate kinase domain of PSD-95 interacts with the SAPAP/GKAP proteins, which in turn bind to the SHANK proteins.

Similarly, mGC is linked to the SHANK platform, at least in part via Homer. The mGC (Farr et al., 2004), analyzed after immunoisolation of mGluR5 and associated molecules, includes SHANK and Homer proteins, both of which have been previously associated with metabotropic glutamate receptors using other methods. Homer proteins bind the cytoplasmic domain of mGlu receptors (Brakeman et al., 1997) and couple mGlu receptors—and hence the mGC—to the SHANK platform (Tu et al., 1999). As SHANK proteins are able to bind to the IP3 receptor, this interaction also links mGlu receptors to the IP3 receptor (Sala et al., 2005).

Finally, the components of the ARC are bound to the SHANK platform. There is evidence for a direct interaction between the GluR1 AMPA receptor and SHANK3 (Uchino et al., 2006). Moreover, there is evidence for an indirect interaction in which transmembrane AMPA regulatory protein (TARP) subunits, including stargazin, bind both AMPA receptors and PSD-95 (e.g., Bats et al., 2007). The interaction of AMPA receptors with PSD-95 in turn allows for the linking of AMPA receptors with the SHANK platform via SAPAP/GKAP.

There are additional important interactions that involve the SHANK platform, but even focusing on these three protein complexes, NRC, mGC, and ARC, it is clear that the SHANK proteins are critically involved in the molecular architecture of glutamatergic synapses. Moreover, as SHANK proteins also interact with F-actin (the major cytoskeletal component of spines) through cortactin (Naisbitt et al., 1999) and additional mechanisms (see Boeckers, 2006), the SHANK platform is also likely involved in the dynamic remodeling of glutamatergic synapses over short and longer time frames (e.g., Hering and Sheng, 2003).

Modulation of SHANK3 expression and synapse formation. Overexpression of SHANK1 leads to increased spine size in neurons in culture (Sala et al., 2001). This effect, which could be further enhanced with the cotransfection of Homer 1, also led to the recruitment of Homer, PSD-95, and GKAP to the spines, along with glutamate receptors, the 1P3 receptor, and F-actin and bassoon, with enhancement of synaptic function, as measured electrophysiologically (Sala et al., 2001). More recent studies with SHANK3 support these conclusions (Roussignol et al., 2005). Thus, introduction of an siRNA construct inhibiting SHANK3 expression led to reduced number of spines in hippocampal neurons in culture. Furthermore, Roussignol et al. (2005) demonstrated that the introduction of SHANK3 into aspiny cerebellar neurons was sufficient to induce functional dendritic spines in these cells, which then express functional NMDA and AMPA receptors. Altogether, these studies in cultured cells support a critical role for SHANK proteins in the development and function of the PSD and the glutamatergic synapse.

Recently, SHANK1 homozygous knockout mice were described which showed alterations in PSD thickness and PSD protein make-up, changes in spine morphology, and decrease glutamatergic synaptic strength (but no changes in long term potentiation (LTP)) (Hung et al. 2008). These changes were associated with an increase in anxiety behavior, deficiencies on rotarod, impaired memory in a contextual fear task and in retention in a radial maze, but increased acquisition in the radial maze, confirming a role for SHANK proteins in glutamatergic transmission and behavior.

Regulation of SHANK3 expression by methylation. Proper expression of SHANK3 is an important element of spine formation and brain development. Methylation of genes is one important means of regulating expression. Interestingly, in a genome-wide analysis, SHANK3 was identified as one of several genes where there was a clear relationship between methylation status at CpG islands in the gene and expression (Ching et al., 2005). The authors demonstrated that SHANK3 is expressed in brain tissue, where the gene is predominantly unmethylated, and not expressed in lymphocytes, where the CpG island studied in the SHANK3 gene was nearly completely methylated.

The study of Ching et al. (2005) was followed by a more recent study that looked in greater detail at SHANK3 as well as at the CpG islands in SHANK1 and SHANK2 (Beni et al., 2007). The authors identified 5 CpG islands in SHANK3 (one of which—identified by Beni et al. (2007) as CpG 4—was the CpG island studied by Ching et al., 2005) and an equivalent number in SHANK1 and SHANK2. Only SHANK3 demonstrated tissue-specific methylation of CpG islands, with a relationship between methylation and tissue-specific expression. These studies demonstrated not only that methylation at several of the CpG islands of SHANK3 correlated with SHANK3 expression, but also that modulating the methylation of SHANK3 in cells in culture altered SHANK3 expression. Thus, treating primary neuronal cultures with methionine to increase methylation resulted in decreased expression of SHANK3, while treating HeLa cells with the demethylating agent 5-AdC resulted in decreased methylation of SHANK3 and increased expression of this gene in these cells, which do not normally express SHANK3. Significantly, the decreased expression of SHANK3 in primary neurons treated with methionine was associated with decreased numbers of dendritic spines and with decreased spine width, similar to what was observed by this same group with siRNA treatment of such cells (see above and Roussignol et al., 2005).

It has been shown that a proportion (0.5-1%) of children diagnosed with autism or autism spectrum disorders have deletions, duplications or mutations in SHANK3. While individuals with a diagnosis of 22q13 deletion syndrome are relatively rare, autism and autism spectrum disorders occur with a frequency of about 1 in 100 children. Considering this, as well as the rates of intellectual disability syndromes in the population, it can be estimated that at least $\frac{1}{6,000}$-$\frac{1}{16,000}$ individuals will have deletions, duplications or mutations in SHANK3 with associated phenotypes. This translates to ~20-60,000 individuals in the USA alone with life-long disability due to alterations in SHANK3 expression. Thus, there is a compelling need for treatments for subjects with 22q13 deletions or duplications or SHANK3 mutations. The present invention addresses this need.

SUMMARY OF THE INVENTION

The present invention provides methods for treating subjects with 22q13 deletion syndrome or SHANK3 deletion or duplication, SHANK3 mutation or reduced expression of SHANK3, in need thereof, the methods comprising administering to the subject insulin-like growth factor 1 (IGF-1), an active IGF-1 fragment including the tripeptide (1-3)IGF-1 or an analog thereof, growth hormone, or an AMPAkine, or another compound that directly or indirectly enhances glutamate neurotransmission, including by inhibiting inhibitory (most typically γ-aminobutyric acid (GABA)) transmission, in an amount and manner effective to treat a subject with 22q13 deletion syndrome or SHANK3 deletion or duplication, mutation or reduced expression.

The present invention further provides methods for treating subjects with 22q13 deletion syndrome or SHANK3 deletion or duplication, mutation or reduced expression in need thereof, the methods comprising administering to the subject an agent that activates the growth hormone receptor, or a downstream signaling pathway thereof, or the insulin-like growth factor 1 (IGF-1) receptor, or a downstream signaling pathway thereof, or a downstream signaling pathway of (1-3) IGF-1, in an amount and manner effective to treat a subject with 22q13 deletion syndrome or SHANK3 deletion or duplication, mutation or reduced expression.

The present invention also provides methods for screening for agents for treating subjects with 22q13 deletion syndrome or SHANK3 deletion or duplication, mutation or reduced expression, the methods comprising determining whether or not the agent enhances long-term potentiation or increases glutamate transmission, wherein an agent that enhances long-term potentiation or increases glutamate transmission is a candidate for treating a subject with 22q13 deletion syndrome or SHANK3 deletion or duplication, mutation or reduced expression, whereas an agent that does not enhance long-term potentiation or increase glutamate transmission is not a candidate for treating a subject with 22q13 deletion syndrome or SHANK3 deletion or duplication, mutation or reduced expression.

The present invention also provides methods for screening for agents for treating subjects with 22q13 deletion syndrome or SHANK3 deletion or duplication, mutation or reduced expression, the methods comprising determining whether or not the agent activates the growth hormone receptor, or a downstream signaling pathway thereof, or the insulin-like growth factor 1 (IGF-1) receptor, or a downstream signaling pathway thereof, or a downstream signaling pathway of (1-3) IGF-1, wherein an agent that activates the growth hormone receptor, or a downstream signaling pathway thereof, or the insulin-like growth factor 1 (IGF-1) receptor, or a downstream signaling pathway thereof, or a downstream signaling pathway of (1-3)IGF-1 is a candidate for treating a subject with 22q13 deletion syndrome or SHANK3 deletion or duplication, mutation or reduced expression, whereas an agent that does not activate the growth hormone receptor, or a downstream signaling pathway thereof, or the insulin-like growth factor 1 (IGF-1) receptor, or a downstream signaling pathway thereof, or a downstream signaling pathway of (1-3)IGF-1 is not a candidate for treating a subject with 22q13 deletion syndrome or SHANK3 deletion or duplication, mutation or reduced expression.

BRIEF DESCRIPTION OF THE DRAWINGS

FIG. 10A-10B. Recombinant human IGF-1 (rhIGF-1) reverses deficits in long-term potentiation and basal synaptic properties at Schaffer collateral-CA1 synapses in Shank3 heterozygous mice in a dose-dependent fashion. rhIGF-1 is administered daily via i.p. injections (120 or 240 μg/kg body weight) starting at P13-15 and continued for 2 weeks for electrophysiological recordings. A. LTP was induced with high-frequency stimulation and normalized field EPSP slope was plotted as a function of time. Vehicle-treated heterozygotes showed reduced LTP, which was reversed by the higher, but not the lower dose of rhIGF-1 (ANOVA, F(2,11)=14.39, p=0.002). The inset shows representative EPSP traces at 90 min after LTP induction from saline-injected (1) and rhIGF-1-injected (2) heterozygous mice (scale bar: 0.5 mV, 10 ms). B. AMPA receptor responses were assessed in the mice. Slices were incubated in the presence of APV and mean field EPSP slope as a function of fiber volley is shown for slices derived from wildtype (WT), Shank3 heterozygous (Het) mice, and Het injected with rhIGF-1. Deficits in AMPA receptor signaling observed in Shank3 heterozygotes were reversed with 2-week rhIGF-1 treatment.

Figure 11:
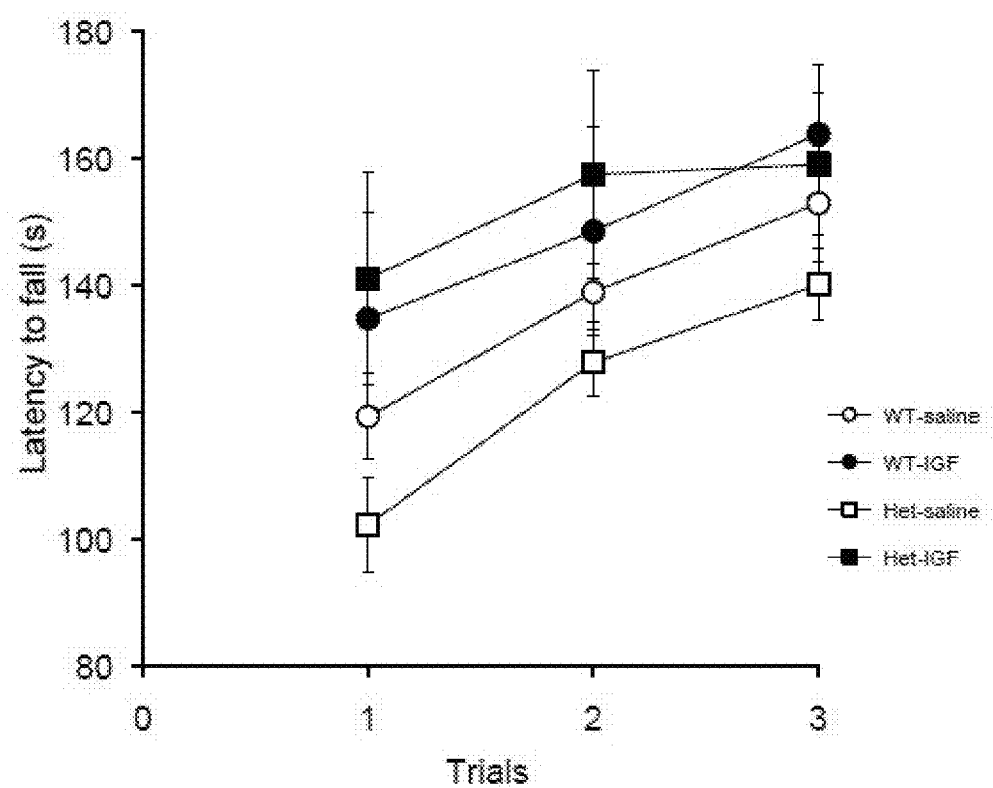

FIG. 11. IGF-1 treatment reverses motor deficits in Shank3 heterozygous mice. Male wildtype (WT) and Shank3 heterozygous (Het) mice, treated with vehicle or recombinant human IGF-1 were tested for motor performance and learning by measuring latencies to fall off a rotating rod. Mice were challenged with three 2-minute trials (each separated by 15 minutes) where the rotation was gradually increased from 0 to 45 rpm. Heterozygous mice injected with saline exhibit reduced latencies to fall compared to wildtype mice. After IGF-1 treatment, heterozygous mice exhibit significantly longer latencies in comparison to vehicle-injected mice of the same genotype.

DETAILED DESCRIPTION OF THE INVENTION

The present invention provides a method for treating a subject with 22q13 deletion syndrome or SHANK3 deletion or duplication, SHANK3 mutation or reduced expression of SHANK3, in need thereof, the method comprising administering to the subject insulin-like growth factor 1 (IGF-1), an active IGF-1 fragment comprising the tripeptide (1-3)IGF-1 or an analog thereof, growth hormone, or an AMPAkine, or another compound that directly or indirectly enhances glutamate neurotransmission, including by inhibiting inhibitory (most typically GABA) transmission, in an amount and manner effective to treat a subject with 22q13 deletion syndrome or SHANK3 deletion or duplication, mutation or reduced expression. Reduced SHANK3 expression can be due, for example, to abnormal methylation of the gene encoding SHANK3.

The invention thus provides a method for treating a subject with 22q13 deletion syndrome or SHANK3 deletion or duplication, SHANK3 mutation or reduced expression of SHANK3, the method comprising administering to the subject insulin-like growth factor 1 (IGF-1) or an active IGF-1 fragment including the tripeptide (1-3)IGF-1 or an analog thereof, in an amount and manner effective to treat a subject with 22q13 deletion syndrome or SHANK3 deletion or duplication, mutation or reduced expression, wherein the subject has autism spectrum disorder, autism, Asperger syndrome, pervasive developmental disorder, mental retardation, hypotonia, a speech deficit, or developmental delay and/or defects.

The invention further provides a method for treating a subject with autism spectrum disorder, autism or Asperger syndrome comprising administering to the subject insulin-like growth factor 1 (IGF-1) or an active IGF-1 fragment including the tripeptide (1-3)IGF-1 or an analog thereof, in an amount and manner effective to treat a subject with autism spectrum disorder, autism, or Asperger syndrome.

The present invention also provides a method for treating a subject with 22q13 deletion syndrome or SHANK3 deletion or duplication, mutation or reduced expression in need thereof, the method comprising administering to the subject an agent that activates the growth hormone receptor, or a downstream signaling pathway thereof, or the insulin-like growth factor 1 (IGF-1) receptor, or a downstream signaling pathway thereof, or a downstream signaling pathway of (1-3) IGF-1, in an amount and manner effective to treat a subject with 22q13 deletion syndrome or SHANK3 deletion or duplication, mutation or reduced expression. As discussed herein, growth hormone stimulates production of IGF-1, and the main downstream signaling pathways of the IGF-1 receptor are the phosphoinositide 3-kinase (PI3K), 3-phosphoinositide-dependent protein kinase 1 (PDK), Akt, mammalian target of rapamycin (mTOR), and extracellular-signal-regulated kinase (ERK) pathways. Examples of such agents include growth hormone, insulin-like growth factor 1 (IGF-1), the tripeptide (1-3)IGF-1 and analogs thereof.

As used herein, to treat a subject with 22q13 deletion syndrome or SHANK3 deletion or duplication, SHANK3 mutation or reduced expression of SHANK3 means to alleviate a sign or symptom associated with 22q13 deletion syndrome or SHANK3 deletion or duplication, mutation or reduced expression. The syndrome is characterized by general hypotonia, motor deficits, absent to delayed speech, and global developmental delays. Individuals with a 22q13 deletion or SHANK3 mutation can suffer from a range of symptoms, with mild to very serious physical and behavioral characteristics. Possible symptoms include, but are not limited to, absent to severely delayed speech; hypotonia; increased tolerance to pain; thin, flaky toenails; ptosis; poor thermoregulation; chewing non-food items; teeth grinding; autistic behaviors; tongue thrusting; hair pulling; aversion to clothes; as well as other physical and behavioral symptoms, including autism spectrum disorders and atypical schizophrenia.

The present invention also provides a method for screening for agents for treating a subject with 22q13 deletion syndrome or SHANK3 deletion or duplication, mutation or reduced expression, the method comprising determining whether or not the agent enhances long-term potentiation or increases glutamate transmission, wherein an agent that enhances long-term potentiation or increases glutamate transmission is a candidate for treating a subject with 22q13 deletion syndrome or SHANK3 deletion or duplication, mutation or reduced expression, whereas an agent that does not enhance long-term potentiation or increase glutamate transmission is not a candidate for treating a subject with 22q13 deletion syndrome or SHANK3 deletion or duplication, mutation or reduced expression. The assay can be carried out, for example, using mice with a disruption of at least one copy of SHANK3 (e.g., Shank3 heterozygous mice).

The present invention also provides a method for screening for agents for treating a subject with 22q13 deletion syndrome or SHANK3 deletion or duplication, mutation or reduced expression, the method comprising determining whether or not the agent activates the growth hormone receptor, or a downstream signaling pathway thereof, or the insulin-like growth factor 1 (IGF-1) receptor, or a downstream signaling pathway thereof, or a downstream signaling pathway of (1-3)IGF-1, wherein an agent that activates the growth hormone receptor, or a downstream signaling pathway thereof, or the insulin-like growth factor 1 (IGF-1) receptor, or a downstream signaling pathway thereof, or a downstream signaling pathway of (1-3)IGF-1 is a candidate for treating a subject with 22q13 deletion syndrome or SHANK3 deletion or duplication, mutation or reduced expression, whereas an agent that does not activate the growth hormone receptor, or a downstream signaling pathway thereof, or the insulin-like growth factor 1 (IGF-1) receptor, or a downstream signaling pathway thereof, or a downstream signaling pathway of (1-3) IGF-1 is not a candidate for treating a subject with 22q13 deletion syndrome or SHANK3 deletion or duplication, mutation or reduced expression. Downstream signaling pathways of the IGF-1 receptor include the PI3K, PDK, Akt, mTOR and ERK pathways.

The assays can be carried out, for example, using a brain slice preparation, such as a hippocampal slice preparation, such as, for example, described herein in Experimental Details. Preferably, the brain slice is from an animal, such as a mouse, with a disruption of at least one copy of SHANK3 (e.g., a Shank3 heterozygous mouse).

Growth hormone (GH) is a protein based polypeptide hormone which stimulates growth and cell reproduction and regeneration in humans and other animals. Growth hormone is synthesized, stored, and secreted by the somatotroph cells in the anterior pituitary gland. Growth hormone is used clinically to treat children's growth disorders and adult growth hormone deficiency. Growth hormone stimulates production of IGF-1. Growth hormone can refer either to the natural hormone produced by the pituitary or biosynthetic growth hormone for therapy. Somatotropin refers to the growth hormone produced naturally in animals, whereas the term somatropin refers to growth hormone produced by recombinant DNA technology. In preferred embodiments, growth hormone is human growth hormone having the amino acid sequence (SEQ ID NO:1) (Accession AAH90045)

```
  1 matgsrtsll lafgllclpw lqegsafpti plsrlfdnam lrahrlhqla
    fdtyqefeea
 61 yipkeqkysf lqnpqtslcf sesiptpsnr eetqqksnle llrisllliq
    swlepvqflr
121 svfanslvyg asdsnvydll kdleegiqtl mgrledgspr tgqifkq-
    tys kfdtnshndd
181 allknyglly cfrkdmdkve tflrivqcrs vegscgf
``` or recombinant human growth hormone having the amino acid sequence (SEQ ID NO:2)

```
  1 fptiplsrlf dnamlrahrl hqlafdtyqe feeayipkeq kysflqnpqt
    slcfsesipt
 61 psnreetqqk snlellrisl lliqswlepv qflrsvfans lvygasdsnv
    ydllkdleeg
121 iqtlmgrled gsprtgqifk qtyskfdtns hnddallkny gllyc-
    frkdm dkvetflriv
181 qcrsvegscg f.
```

Recombinant human growth hormone is available, e.g., from Cell Sciences®, Canton Mass. (Catalog No. CRH200A-C) (SEQ ID NO:2).

Insulin-like growth factor 1 (IGF-1), also known as somatomedin C or mechano growth factor, is a protein that is encoded by the IGF1 gene in humans. IGF-1 is a hormone similar in molecular structure to insulin. It plays an important role in childhood growth and continues to have an anabolic effect in adults. A synthetic analog of IGF-1, mecasermin, is used for the treatment of growth failure. IGF-1 is produced primarily by the liver as an endocrine hormone as well as in target tissues in a paracrine/autocrine fashion. Production is stimulated by growth hormone and can be retarded by under-nutrition, growth hormone insensitivity, lack of growth hormone receptors, or failure of the downstream signaling pathway post growth hormone receptors including SHP2 and STAT5B. IGF-1 has substantial human safety data and is approved for use in children. In preferred embodiment, IGF-1 is recombinant human IGF-1 (a 7.6 kDa protein) having the amino acid sequence (SEQ ID NO:3)

The tripeptide (1-3)IGF-1 has the amino acid sequence glycine-proline-glutamic acid (Gly-Pro-Glu or GPE). (1-3) IGF-1 can be obtained from Bachem (Torrance, Calif.) as H-Gly-Pro-Glu-OH (Catalog No. H-2468). The peptide has the advantage that it can penetrate the blood-brain barrier. Analogs of (1-3)IGF-1 that can be used include, but are not limited to, (1-3) IGF-1 amide, (1-3) IGF-1 stearate, Gly-Pro-Dglutamate, glycine-proline-threonine (Gly-Pro-Thr), glycine-glutamic acid-proline (Gly-Glu-Pro), glutamic acid-glycine-proline (Glu-Gly-Pro), and glutamic acid-proline-glycine (Glu-Pro-Gly).

AMPAkines are a class of compounds that strongly interact with glutamergic AMPA (α-amino-3-hydroxyl-5-methyl-4-isoxazolepropionic acid) receptors. Glutamergic AMPA receptors are non-NMDA-type ionotropic transmembrane receptors for glutamate that mediates fast synaptic transmission in the central nervous system (CNS). To date, four structural classes of AMPAkines have been developed: pyrrolidine derivatives of racetam drugs such as piracetam and aniracetam; CX-series of drugs encompassing a range of benzoylpiperidine and benzoylpyrrilidine structures; benothiazide derivatives such as cyclothiazide and IDRA-21; and biaryl-propylsulfonamides such as LY-392,098, LY-404,187, LY-451,646, and LY-503,430. AMPAkines bind to glutamergic AMPA receptors, boosting the activity of glutamate, a neurotransmitter, and making it easier to encode memory and learning. Some AMPAkines may increase levels of trophic factors such as brain-derived neurotrophic factor. Preferred AMPAkines include CX AMPAkines (Cortex Pharmaceuticals, Inc., Irvine, Calif.), such as for example CX-516 (Ampalex), CX-546, CX-614, CX-691 (Farampator), CX-717, CX-701, CX-1739, CX-1763 and CX-1837 (see, e.g., U.S. Pat. Nos. 5,650,409, 5,736,543, 5,985,871, 6,166,008, 6,313,115, and 7,799,913, and U.S. Patent Application Publications No. 2002/0055508, 2010/0041647, 2010/0173903, 2010/0267728, 2010/02866177, and 2011/0003835, the contents of which are herein incorporated by reference).

Compounds that directly or indirectly enhance glutamate neurotransmission including, for example, by inhibiting inhibitory (most typically GABA) transmission, include, for example, glycine transporter 1 (GLYT1) inhibitors, brain-derived neurotrophic factor (BDNF), and cyclothiazide. Cyclothiazide acts both on AMPA receptors and GABA(A) receptors. GLYT1 inhibitors are a functional class of compounds and include compounds that act as GABA(A) receptor negative allosteric modulators and inhibitors. Specific GLYT1 inhibitors include, for example, NFPS, Org 24461, and sarcosine.

IGF-1 interacts with its receptor (IGF-1R) to initiate downstream responses such as proliferation and differentiation. The IGF-1R is a transmembrane receptor that is activated by IGF-1 and by the related growth factor IGF-2. It belongs to the large class of tyrosine kinase receptors and mediates the effects of IGF-1. Tyrosine kinase receptors, including the IGF-1R, mediate their activity by causing the addition of a phosphate group to particular tyrosines on certain proteins within a cell. This addition of phosphate induces what are called "cell signaling" cascades - and the usual result of activation of the IGF-1R is survival and proliferation in mitosis-competent cells, and growth (hypertrophy) in tissues such as skeletal muscle and cardiac muscle. IGF-1R activates sev-

```
  1 gpetlcgael vdalqfvcgd rgfyfnkptg ygsssrrapq tgivdeccfr scdlrrlemy
 61 caplkpaksa.
``` eral downstream signaling pathways. The main downstream signaling pathways of IGF-1R are the PI3K, PDK, Akt, mTOR and ERK pathways.

Phosphoinositide 3-kinases (PI 3-kinases or PI3Ks) are a family of enzymes involved in cellular functions such as cell growth, proliferation, differentiation, motility, survival and intracellular trafficking PI3Ks are downstream of IGF-1R and interact with the IRS (Insulin receptor substrate) in order to regulate cell function uptake through a series of phosphorylation events. The phosphoinositol-3-kinase family is divided into three different classes: Class I, Class II, and Class III. The classifications are based on primary structure, regulation, and in vitro lipid substrate specificity. PI3K has also been implicated in Long-term potentiation (LTP). PI3Ks are necessary for the survival of progenitors and mature oligodendrocytes and for the IGF-1-mediated cell survival, proliferation, and protein synthesis.

AKT protein family, which members are also called protein kinases B (PKB) plays an important role in mammalian cellular signaling. In humans, there are three genes in the "Akt family": Akt1, Akt2, and Akt3. These genes code for enzymes that are members of the serine/threonine-specific protein kinase family. Akt1 is involved in cellular survival pathways, by inhibiting apoptotic processes. Akt1 is also able to induce protein synthesis pathways, and is therefore a key signaling protein in the cellular pathways that lead to skeletal muscle hypertrophy, and general tissue growth. Akt2 is an important signaling molecule in the insulin signaling pathway. It is required to induce glucose transport. Akt can be phosphorylated by PDK1 and mTORC2. Beside downstream effectors of PI3K, Akt can be activated in a PI3K-independent manner. Akt2 is required for the insulin-induced translocation of glucose transporter 4 (GLUT4) to the plasma membrane. Glycogen synthase kinase 3 (GSK-3) could be inhibited upon phosphorylation by Akt, which results in promotion of glycogen synthesis. Akt inhibitors and dominant-negative Akt expression can block IGF-1 stimulated protein synthesis in oligodendrocyte progenitors.

3-phosphoinositide dependent protein kinase-1 (PDK1) is a protein which in humans is encoded by the PDPK1 gene and is a master kinase crucial for the activation of AKT/PKB and many other AGC kinases including PKC, S6K, and SGK. An important role for PDK1 is in the signalling pathways activated by several growth factors and hormones including insulin signalling. PDK1 functions downstream of PI3K through PDK1's interaction with membrane phospholipids including phosphatidylinositols, phosphatidylinositol(3,4)-bisphosphate and phosphatidylinositol(3,4,5)-trisphosphate. PI3K indirectly regulates PDPK1 by phosphorylating phosphatidylinositols which in turn generates phosphatidylinositol(3,4)-bisphosphate and phosphatidylinositol(3,4,5)-trisphosphate.

The mammalian target of rapamycin (mTOR), also known as mechanistic target of rapamycin or FK506 binding protein 12-rapamycin associated protein 1 (FRAP1), is a protein which in humans is encoded by the FRAP1 gene. mTOR is a serine/threonine protein kinase that regulates cell growth, cell proliferation, cell motility, cell survival, protein synthesis, and transcription. mTOR integrates the input from upstream pathways, including insulin, growth factors (such as IGF-1 and IGF-2), and mitogens. mTOR also senses cellular nutrient and energy levels and redox status.

Extracellular-signal-regulated kinases (ERKs), or classical MAP kinases, are widely expressed protein kinase intracellular signalling molecules that are involved in functions including the regulation of meiosis, mitosis, and postmitotic functions in differentiated cells. Many different stimuli, including growth factors (such as IGF-1 and IGF-2), cytokines, virus infection, ligands for heterotrimeric G protein-coupled receptors, transforming agents, and carcinogens, activate the ERK pathway.

The 22q13 deletion syndrome or SHANK3 deletion or duplication, mutation or reduced expression can be treated by local or systemic administration of the IGF-1, IGF-1-derived peptide or analog, growth hormone, AMPAkine, or other compound that directly or indirectly enhances glutamate neurotransmission, including by inhibiting inhibitory (most typically GABA) transmission, or other therapeutic agent. Local treatment may comprise intramuscular or intratissue injection. Systemic treatment may comprise enteral or intravenous methods. The IGF-1, IGF-1-derived peptide or analog, growth hormone, AMPAkine, or other compound that directly or indirectly enhances glutamate neurotransmission, including by inhibiting inhibitory (most typically GABA) transmission, or agent may be administered in a pharmaceutical composition comprising the IGF-1, IGF-1-derived peptide or analog, growth hormone, AMPAkine, or other compound that directly or indirectly enhances glutamate neurotransmission, including by inhibiting inhibitory (most typically GABA) transmission, or agent in a pharmaceutically acceptable carrier.

The pharmaceutically acceptable carrier must be compatible with the IGF-1, IGF-1-derived peptide or analog, growth hormone, AMPAkine, or other compound that directly or indirectly enhances glutamate neurotransmission, including by inhibiting inhibitory (most typically GABA) transmission, or agent, and not deleterious to the subject. Examples of acceptable pharmaceutical carriers include carboxymethylcellulose, crystalline cellulose, glycerin, gum arabic, lactose, magnesium stearate, methylcellulose, powders, saline, sodium alginate, sucrose, starch, talc, and water, among others. Formulations of the pharmaceutical composition may conveniently be presented in unit dosage and may be prepared by any method known in the pharmaceutical art. For example, the IGF-1, IGF-1-derived peptide or analog, growth hormone, AMPAkine, or other compound that directly or indirectly enhances glutamate neurotransmission, including by inhibiting inhibitory (most typically GABA) transmission, or agent may be brought into association with a carrier or diluent, as a suspension or solution. Optionally, one or more accessory ingredients, such as buffers, flavoring agents, surface-active ingredients, and the like, may also be added. The choice of carriers will depend on the method of administration. The pharmaceutical composition can be formulated for administration by any method known in the art, including but not limited to, intravenously and intracranially.

The amount of IGF-1, IGF-1-derived peptide or analog, growth hormone, AMPAkine, or other compound that directly or indirectly enhances glutamate neurotransmission, including by inhibiting inhibitory (most typically GABA) transmission, or agent therapeutically necessary will depend on the severity of the 22q13 deletion syndrome or SHANK3 mutation as well as the manner of administration of the IGF-1, IGF-1-derived peptide or analog, growth hormone, AMPAkine, or other compound that directly or indirectly enhances glutamate neurotransmission, including by inhibiting inhibitory (most typically GABA) transmission, or agent. One skilled in the art can easily determine the amount and manner of administration of IGF-1, IGF-1-derived peptide or analog, growth hormone, AMPAkine, or other compound that directly or indirectly enhances glutamate neurotransmission, including by inhibiting inhibitory (most typically GABA) transmission, or agent necessary.

According to the method of the present invention, the IGF-1, IGF-1-derived peptide or analog, growth hormone, AMPAkine, or other compound that directly or indirectly enhances glutamate neurotransmission, including by inhibiting inhibitory (most typically GABA) transmission, or other therapeutic agent may be administered to a subject by any known procedure including, but not limited to, oral administration, parenteral administration, transdermal administration, intranasal administration, and administration through an osmotic mini-pump.

For oral administration, the formulation of the IGF-1, IGF-1-derived peptide or analog, growth hormone, AMPAkine, or other compound that directly or indirectly enhances glutamate neurotransmission, including by inhibiting inhibitory (most typically GABA) transmission, or other therapeutic agent may be presented as capsules, tablets, powder, granules, or as a suspension. The formulation may have conventional additives, such as lactose, mannitol, corn starch, or potato starch. The formulation may also be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For a parenteral administration, the IGF-1, IGF-1-derived peptide or analog, growth hormone, AMPAkine, or other compound that directly or indirectly enhances glutamate neurotransmission, including by inhibiting inhibitory (most typically GABA) transmission, or other therapeutic agent may be combined with a sterile aqueous solution which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be present in unit or multi-dose containers, such as sealed ampoules or vials. The formulation may be delivered by any mode of injection, including, without limitation, epifascial, intrasternal, intravascular, intravenous, parenchymatous, or subcutaneous.

For transdermal administration, the IGF-1, IGF-1-derived peptide or analog, growth hormone, AMPAkine, or other compound that directly or indirectly enhances glutamate neurotransmission, including by inhibiting inhibitory (most typically GABA) transmission, or other therapeutic agent may be combined with skin penetration enhancers, such as propylene glycol, polyethylene glycol, isopropanol, ethanol, oleic acid, N-methylpyrrolidone, and the like, which increase the permeability of the skin to the IGF-1, IGF-1-derived peptide or analog, growth hormone, AMPAkine, or other compound that directly or indirectly enhances glutamate neurotransmission, including by inhibiting inhibitory (most typically GABA) transmission, or other therapeutic agent. The IGF-1, IGF-1-derived peptide or analog, growth hormone, AMPAkine, or other compound that directly or indirectly enhances glutamate neurotransmission, including by inhibiting inhibitory (most typically GABA) transmission, or other therapeutic agent compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent such as methylene chloride, evaporated to the desired viscosity, and then applied to backing material to provide a patch.

The IGF-1, IGF-1-derived peptide or analog, growth hormone, AMPAkine, or other compound that directly or indirectly enhances glutamate neurotransmission, including by inhibiting inhibitory (most typically GABA) transmission, or other therapeutic agent may also be released or delivered from an osmotic mini-pump. The release rate from an elementary osmotic mini-pump may be modulated with a microporous, fast-response gel disposed in the release orifice. An osmotic mini-pump would be useful for controlling the release of, or targeting delivery of, the IGF-1, IGF-1-derived peptide or analog, growth hormone, AMPAkine, or other compound that directly or indirectly enhances glutamate neurotransmission, including by inhibiting inhibitory (most typically GABA) transmission, or other therapeutic agent.

Long-term potentiation (LTP) is a long-lasting enhancement in signal transmission between two neurons that results from stimulating them synchronously. It is one of several phenomena underlying synaptic plasticity, the ability of chemical synapses to change their strength. LTP shares many features with long-term memory, making it an attractive candidate for a cellular mechanism of learning. For example, LTP and long-term memory are triggered rapidly, each depends upon the synthesis of new proteins, each has properties of associativity, and each can last for many months. LTP may account for many types of learning, from the relatively simple classical conditioning present in all animals, to the more complex, higher-level cognition observed in humans. At a cellular level, LTP enhances synaptic transmission. It improves the ability of two neurons, one presynaptic and the other postsynaptic, to communicate with one another across a synapse.

Chemical synapses are functional connections between neurons throughout the nervous system. In a typical synapse, information is largely passed from the first (presynaptic) neuron to the second (postsynaptic) neuron via a process of synaptic transmission. Through experimental manipulation, a non-tetanic stimulus can be applied to the presynaptic cell, causing it to release a neurotransmitter such as glutamate onto the postsynaptic cell membrane. There, glutamate binds to receptors such as AMPA receptors (AMPARs) embedded in the postsynaptic membrane. The AMPA receptor is one of the main excitatory receptors in the brain, and is responsible for most of its rapid, moment-to-moment excitatory activity. Glutamate binding to the AMPA receptor triggers the influx of positively charged sodium ions into the postsynaptic cell, causing a short-lived depolarization called the excitatory postsynaptic potential (EPSP). Extracellular-signal-regulated kinases (ERKs) play a role in late LTP, where gene expression and protein synthesis is brought about by the persistent activation of protein kinases activated during early LTP. ERK phosphorylates a number of cytoplasmic and nuclear molecules that ultimately result in the protein synthesis and morphological changes observed in late LTP. ERK-mediated changes in transcription factor activity may trigger the synthesis of proteins that underlie the maintenance of L-LTP.

An excitatory postsynaptic potential (EPSP) is a temporary depolarization of postsynaptic membrane potential caused by the flow of positively charged ions into the postsynaptic cell as a result of opening of ligand-sensitive channels. ESPSs in living cells are caused chemically. When an active presynaptic cell releases neurotransmitters into the synapse, some bind to receptors on the postsynaptic cell. Many of these receptors contain an ion channel capable of passing positively charged ions either into or out of the cell. The depolarizing current causes an increase in membrane potential, the ESPS. The amino acid glutamate is the neurotransmitter most often associated with EPSPs.

Glutamate is the most abundant excitatory neurotransmitter in the vertebrate nervous system. At chemical synapses, glutamate is stored in vesicles. Nerve impulses trigger release of glutamate from the pre-synaptic cell. In the opposing post-synaptic cell, glutamate receptors, such as the NMDA receptor, bind glutamate and are activated. Because of its role in synaptic plasticity, glutamate is involved in cognitive functions like learning and memory in the brain. The form of plasticity known as long-term potentiation takes place at glutamatergic synapses in the hippocampus, neocortex, and other parts of the brain. Glutamate does not work only as a point to point transmitter but also through spill-over synaptic crosstalk between synapses in which summation of glutamate released from neighboring synapse creates extrasynaptic signaling/volume transmission.

Glutamate transporters are found in neuronal and glial membranes. They rapidly remove glutamate from the extracellular space. In brain injury or disease, they can work in reverse and excess glutamate can accumulate outside cells. This process causes calcium ions to enter cells via NMDA receptor channels, leading to neuronal damage and eventual cell death, and is called excitotoxicity.

The subject can be any mammal, in particular a human. The subject can have, for example, one or more of autism, Asperger syndrome, autism spectrum disorder, pervasive developmental disorder, mental retardation, hypotonia, speech deficits and developmental delay and/or defects.

Experimental Details

Brief experimental procedures: Hippocampal slices (350 μm) are prepared from 1-3 month old Shank3 heterozygous, Shank3 knockout, and wildtype littermates, treated with (1-3) IGF-1 peptide, full-length IGF1, growth hormone, AMPAkine or saline or other appropriate control. Slices are perfused with Ringer's solution, bubbled with 95% $O_2$/5% $CO_2$, at 32° C., during extracellular recordings. Baseline of field excitatory postsynaptic potentials (fEPSPs) recorded from stratum radiatum in area CA1, evoked by stimulation of the Schaffer collateral-commissural afferents with bipolar tungsten electrodes placed into area CA3. Long-term potentiation (LTP) is induced either by a high-frequency stimulus (four trains of 100 Hz, 1 s stimulation separated by 5 min), or by theta-burst stimulation (TBS) (10 bursts of four pulses at 100 Hz separated by 200 ms), with a success rate >90% for control and genetically-modified animals with all stimulation protocols. To induce long-term depression (LTD), Schaffer collaterals were stimulated by a low frequency stimulus (900 pulses at 1 Hz for 15 min) or paired-pulse low frequency stimulus. LTD was induced with a success rate >90% for control animals. In order to examine Akt phosphorylation hippocampus and cortex are dissected from the other hemisphere from Shank3 heterozygous and wildtype littermates, used to make slices and are immediately snap-frozen on dry ice. Western blot analysis is performed for total- and phospho-Akt levels. Results are presented in FIGS. 1-10. Mice were also tested for motor performance and learning by measuring latencies to fall off a rotating rod. Mice were challenged with three 2-minute trials (each separated by 15 minutes) where the rotation was gradually increased from 0 to 45 rpm, and results are presented in FIG. 11.

Figures 1A, 1B:
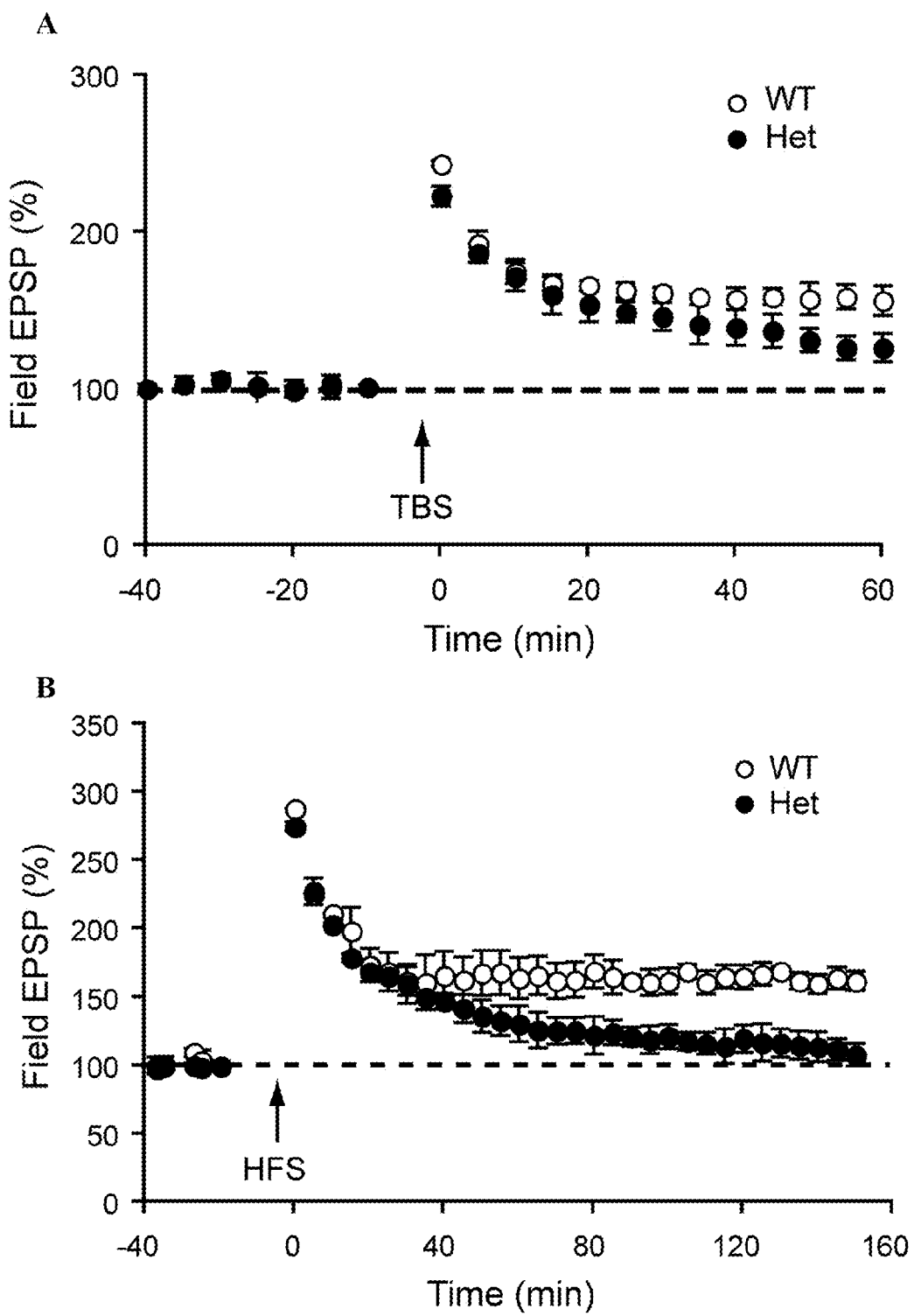
FIG. 1A-1B. Long-term potentiation is impaired in Shank3 heterozygotes. Long-term potentiation (LTP) was induced either by (B) high frequency stimulus (HFS) (4×100 Hz, separated by 5 min) or (A) theta-burst stimulus (TBS) (10 bursts of four pulses at 100 Hz separated by 200 ms) in hippocampal slices in mice. In both conditions, LTP as assessed by field recordings of excitatory postsynaptic potential (EPSP) was impaired in the heterozygous animals (Het) compared to wildtype (WT).
Figure 2A:
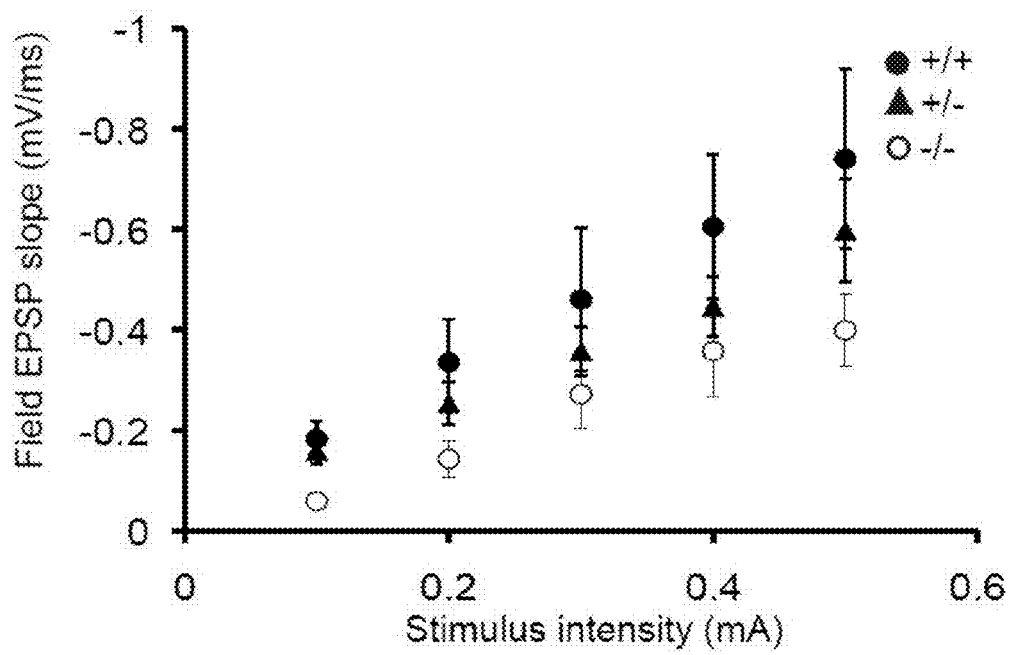
FIG. 2A-2B. Basal synaptic transmission is reduced in Shank3-deficient mice. Mice with a targeted disruption of one copy of the Shank3 gene ("Shank3 heterozygotes") and knockouts were compared to wild type littermate controls. Both the input-output curve (figure) and the amplitude of miniature excitatory postsynaptic currents (EPSCs) (not shown) from hippocampal CA1 pyramidal neurons for Shank3 heterozygotes are significantly lower than those in control mice indicating a reduction in basal transmission due to a postsynaptic effect. (A) Field excitatory postsynaptic potential (fEPSP) slope versus stimulus intensity for wild type (WT), heterozygous (Het), and knockout (KO). Average slope of input-output function: WT (+/+), 1.38±0.3; Het (+/−), 1.07±0.2; KO (−/−), 0.91±0.2, $F_{2,21}=7.30$, p<0.01. (B) Both LTP induction and maintenance is impaired in Shank3 knockouts, indicating a more severe phenotype in the knockout mice. fEPSP slope versus time for WT, Het and KO. In the +/+ control group, fEPSP slope recorded in area CA1 significantly increased over baseline after TBS and was sustained for at least 60 min (154.7±2.9% of baseline at 60 min, 159.3±2.6% at 40 min post-TBS). In Shank3−/− mice, the initial potentiation was significantly lower and decayed rapidly to baseline by 40 min (101.9±2.4% at 40 min post-TBS, N=4-7 mice per genotype, $F(2,14)=85.2$, p<0.001). Shank3+/− mice also showed reduced TBS-induced LTP but normal initial potentiation.
Figure 2B:
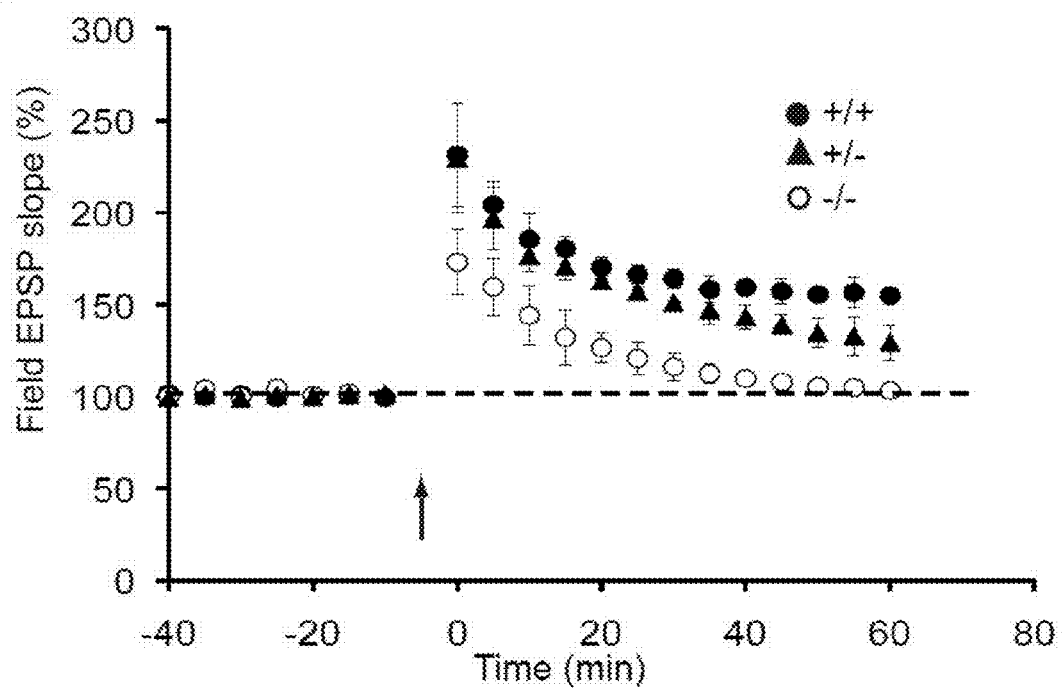
Figures 3A, 3B:
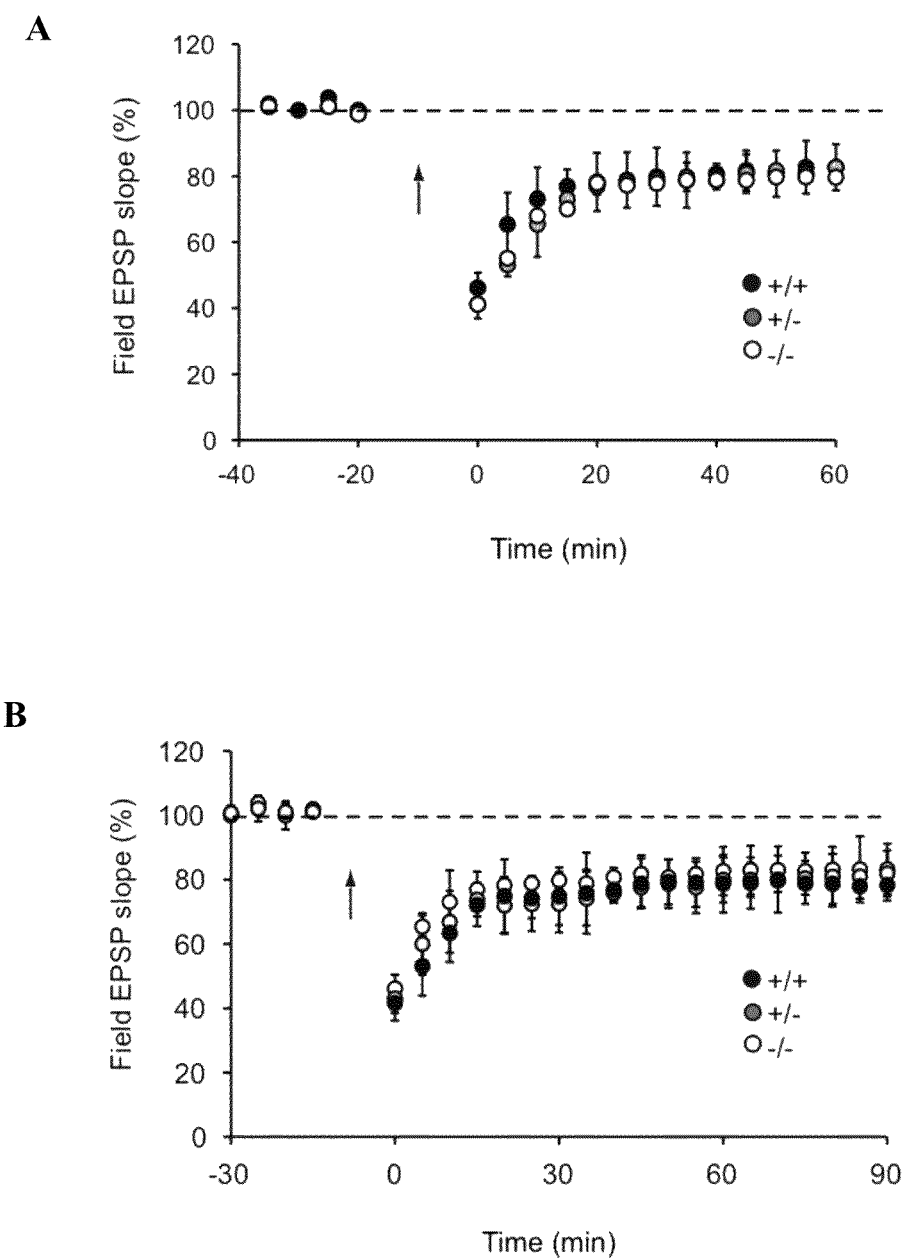
FIG. 3A-3B. Both Shank3 heterozygous and homozygous mice do not show alteration in long-term depression. Long-term depression is induced either by (A) low frequency stimulus (LFS, 900 pulses at 1 Hz; 15 min duration) or (B) paired-pulse low frequency stimulus (PP-LFS, 1 Hz for 20 min; 50 ms interstimulus interval), which is known to induce mGluR-dependent form of long-term depression. N=3 for each group. N=3 for each group.
Figure 4A:
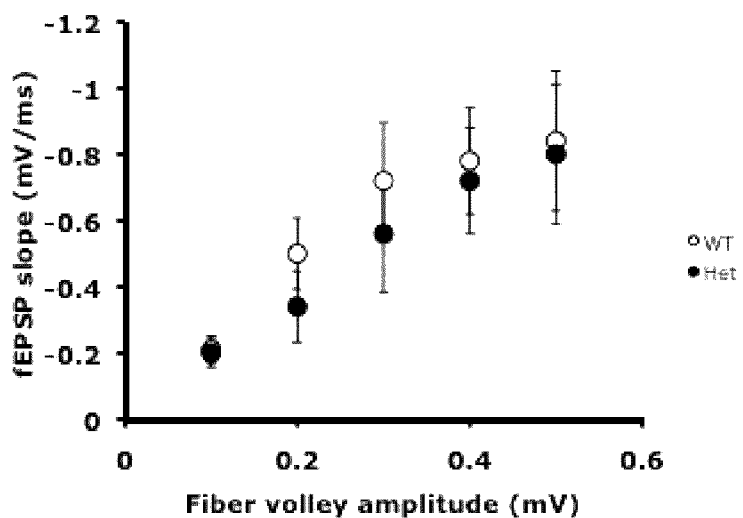
FIG. 4A-4B. Decrease in the AMPA component of fEPSP in SHANK3 heterozygotes. (A) fEPSP slope versus fiber volley amplitude for the NMDA component of neurotransmission, carried out in the presence of CNQX, a blocker of AMPA receptors. (B) fEPSP slope versus fiber volley amplitude for the AMPA component of neurotransmission, carried out in the presence of APV, a blocker of NMDA receptors (N=4 mice per genotype, two to three slices per mouse P=0.001).
Figure 4B:
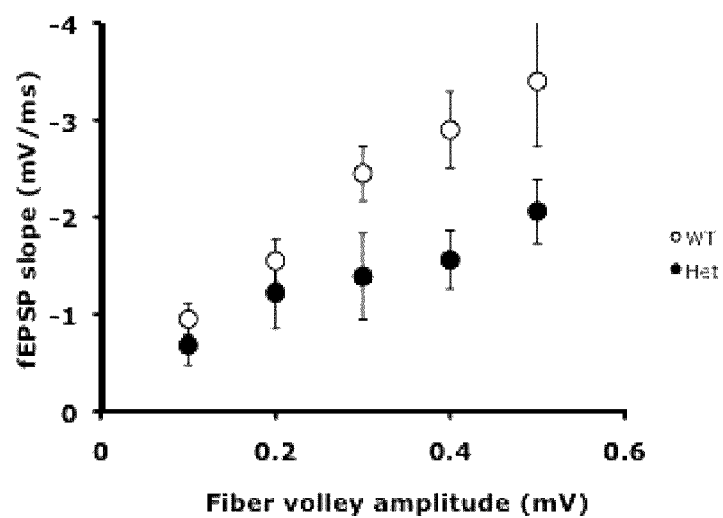
Figure 5A:
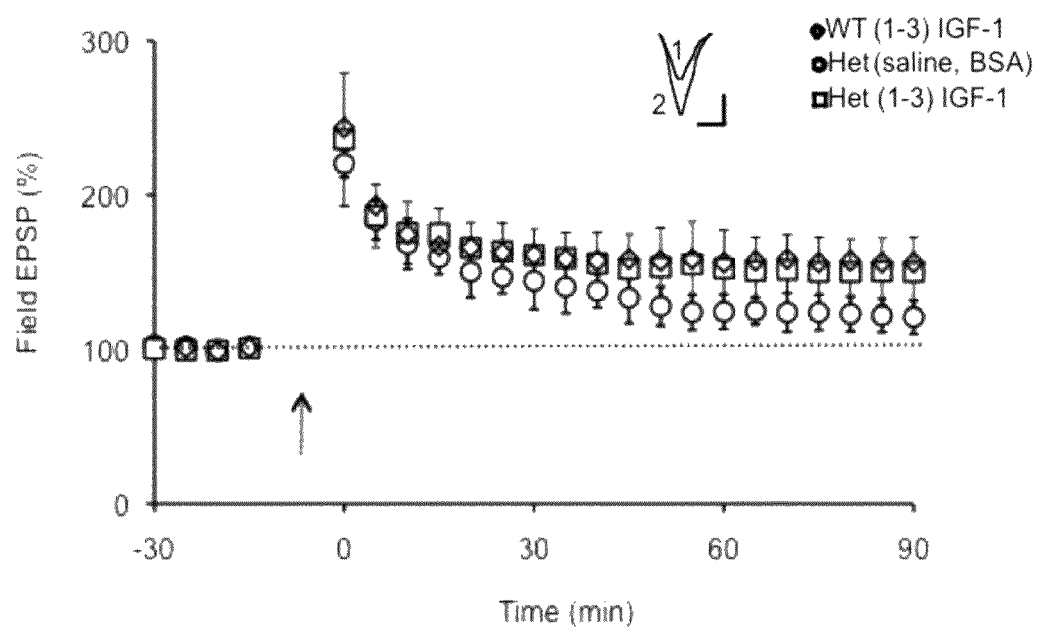
FIG. 5A-5C. Effects of (1-3)IGF-1 treatment on long-term potentiation at Schaffer collateral-CA1 synapses. (1-3)IGF-1 was administered daily via i.p. injections (0.01 mg/g body weight) starting at P13-15 and continuing for 2 weeks for electrophysiological recordings. (A) Hippocampal slices from wildtype (WT) and Shank3 heterozygous (Het) mice injected with vehicle (saline, 0.01% bovine serum albumin (BSA)) or (1-3)IGF-1 were subjected to an LTP inducing stimulation, producing long-lasting potentiation as shown by normalized field EPSP slope as a function of time. Vehicle-treated heterozygotes showed reduced LTP, which was reversed by (1-3)IGF-1 (ANOVA, $F(2,11)=8.98$, p=0.007 at 90 min. The inset shows representative EPSP traces at 90 min after LTP induction from saline-injected (1) and (1-3)IGF-1-injected (2) heterozygous mice (scale bar: 0.5 mV, 10 ms). (B) Input-output curves, plotting field EPSP slopes (mV/ms) as a function of stimulation strength (mA) were significantly suppressed in slices from Shank3 heterozygous mice, but were not different from the wild type in heterozygous mice injected with (1-3)IGF-1. (C) (1-3)IGF-1 peptide (same protocol used in the treatment of heterozygote mice) treatment reversed the impairment in LTP in Shank3 KO mice. fEPSP versus time for KO, KO injected with IGF1 peptide (N=2), and WT mice.
Figure 5B:
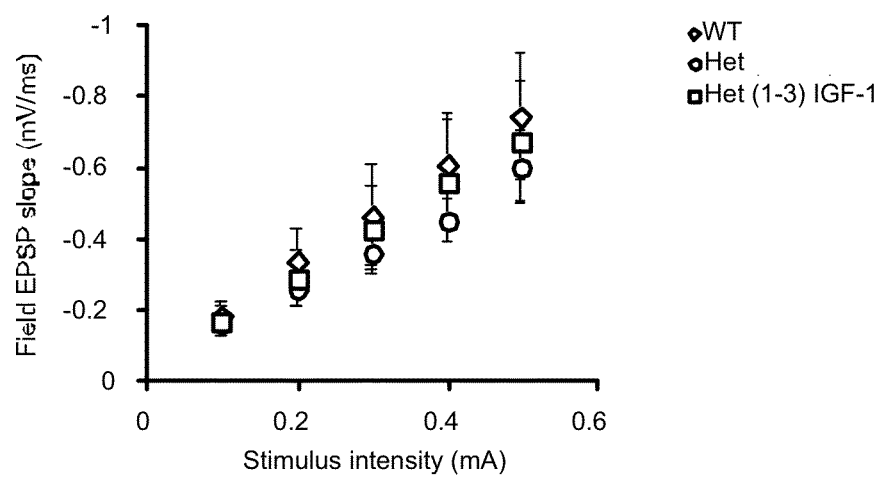
Figure 5C:
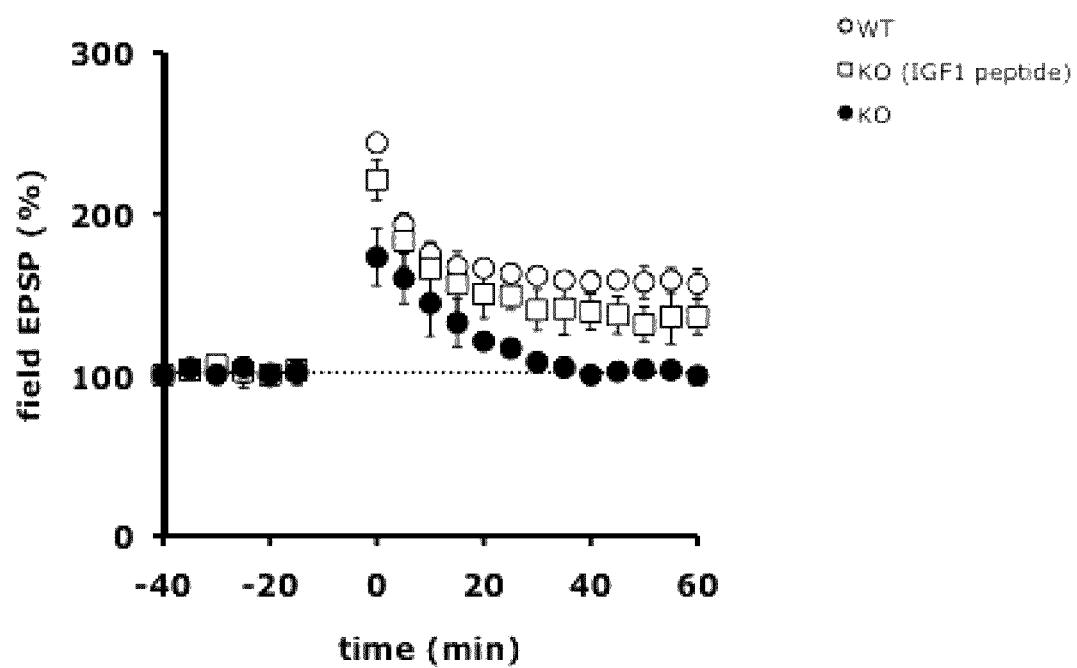
Figure 6:
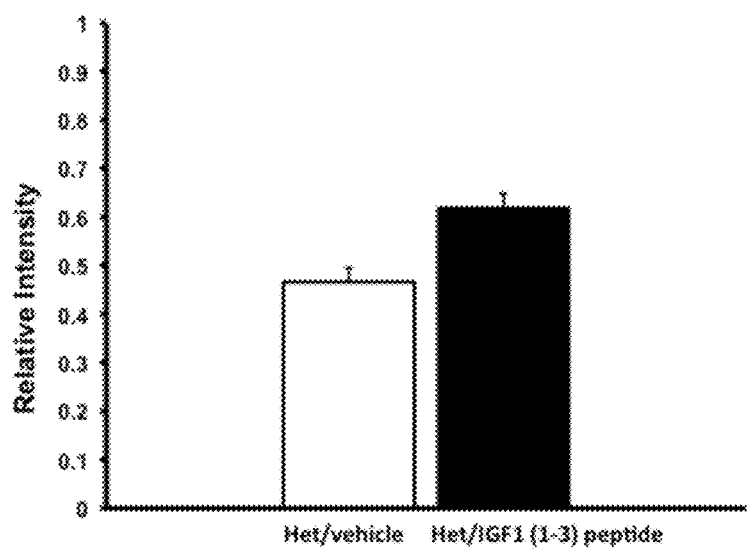
FIG. 6. IGF1 treatment activates PI3K-Akt pathway in the hippocampus. PI3K binds to AMPARs and is required to maintain AMPAR surface expression during long-term potentiation. Figure shows the increase in the phosphorylation of Akt (pAkt1) after IGF1 treatment in heterozygote mice, compared to the vehicle injected mice (n=3, P=0.0366, unpaired t test). The data implicates the PI3K-Akt pathway in the beneficial effects of (1-3)IGF-1.
Figure 6:
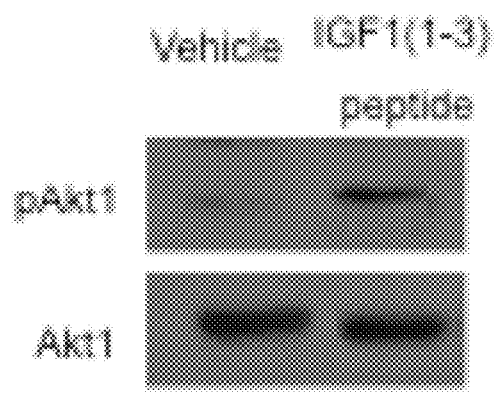
Figure 7:
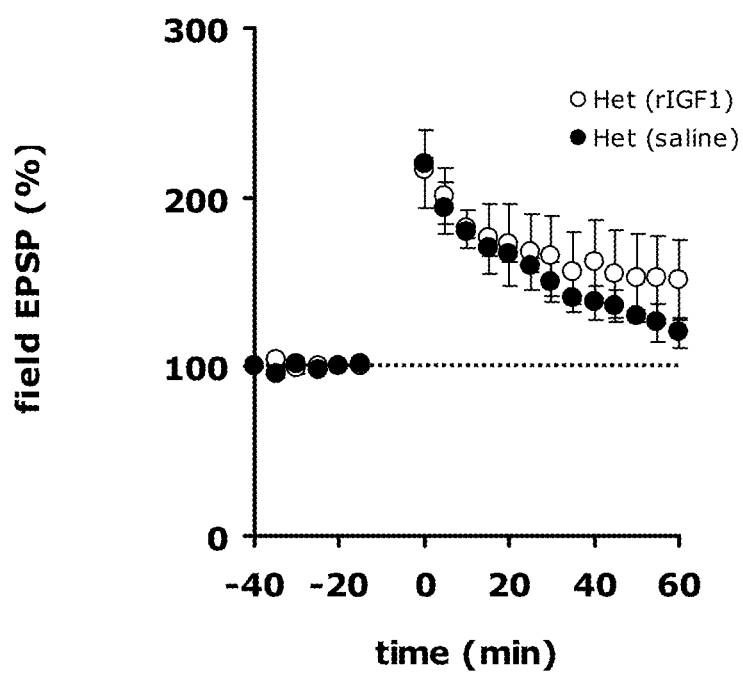
FIG. 7. Effect of intranasal recombinant IGF-1 treatment on field EPSP in Shank3 heterozygotes (Het). Two-week old mice were anesthetized with a mixture of ketamine and xylazine. Recombinant human IGF-1 (rhIGF-1) or saline was administered intranasally at 48 h intervals for a total of 10 doses (15 µl solution containing 60 µg IGF-1 or vehicle per mouse was given over 10-15 min period). N=2.
Figure 8:
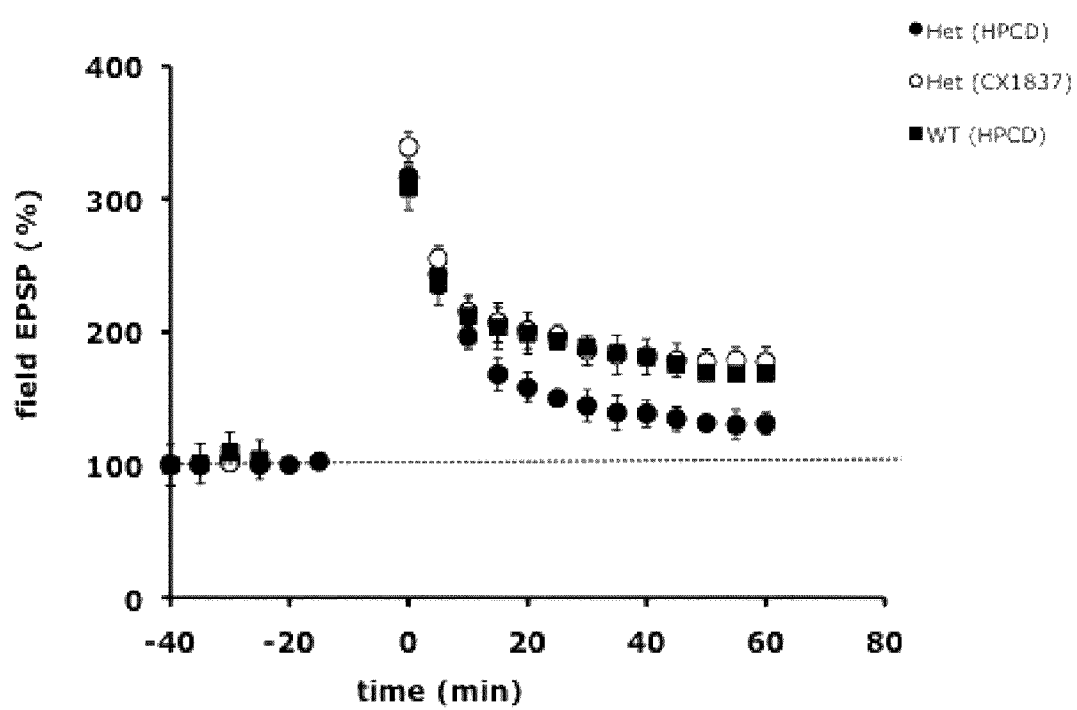
FIG. 8. Ampakine CX1837 restores long-term potentiation in Shank3 heterozygous mice. Effects of CX1837 treatment on long-term potentiation at Schaffer collateral-CA1 synapses in Shank3 heterozygous mice. Ampakine CX1837 or HPCD vehicle is administered daily via i.p. injections (1.5 mg/kg body weight) starting at 2 weeks old and continued for 4 weeks for electrophysiological recordings.
Figure 9:
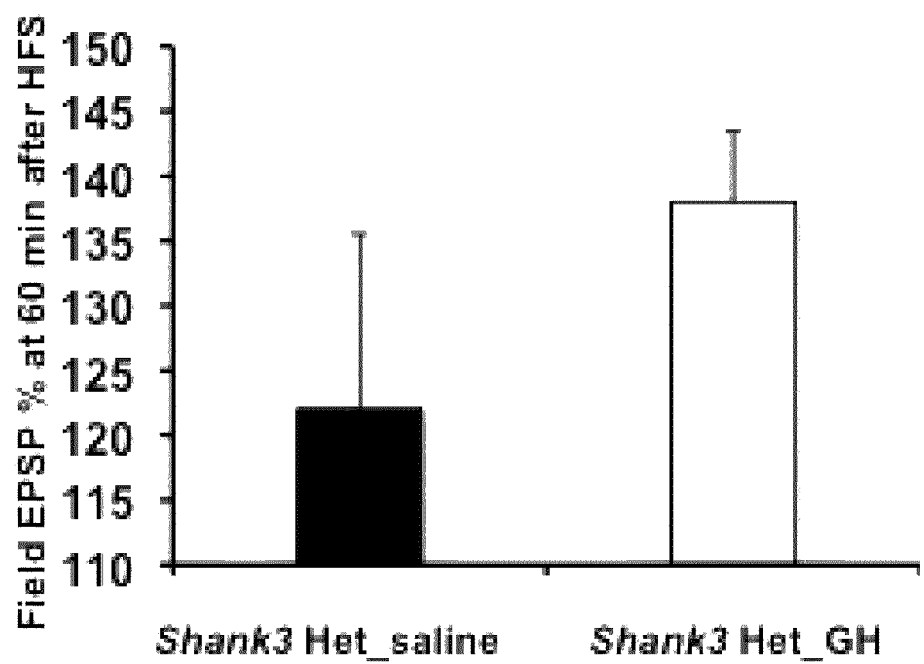
FIG. 9. Effects of growth hormone treatment on long-term potentiation at Schaffer collateral-CA1 synapses in Shank3 heterozygous mice. Growth hormone is administered daily via i.p. injections (1 mg/kg body weight) starting at P13-15 and continued for 2 weeks for electrophysiological recordings.

A mouse with hemizygous loss of full-length Shank3 (Bozdagi et al., 2010) was used to investigate whether IGF-1 could reverse synaptic deficits in a preclinical model. Tests were first made with an active peptide of IGF-1 ((1-3)IGF-1), which has been shown to cross the blood-brain barrier (O'Kusky et al., 2000) and rescue Rett syndrome symptoms in Mecp2-deficient mice. Intraperitoneal injection at 10 μg/g/day for 2 weeks restored normal hippocampal LTP in Shank3 heterozygous mice (FIG. 5a). While LTP was significantly reduced in vehicle treated heterozygotes, heterozygous mice treated with IGF-1 showed a complete rescue. Similarly, LTP at 90 minutes after induction was significantly (P=0.007) reduced in vehicle-treated heterozygotes, compared to wildtype littermates, but not when comparing peptide treated heterozygotes to wildtype animals. In addition, the significantly (P=0.029) reduced input-output (I/O) function observed in heterozygotes [obtained by plotting field excitatory postsynaptic potential (fEPSP) slope versus stimulus intensity], was reversed after 2 weeks administration of active peptide of IGF-1 (FIG. 5b), indicating that deficits in synaptic transmission are rescued by (1-3)IGF-1.

Figure 10A:
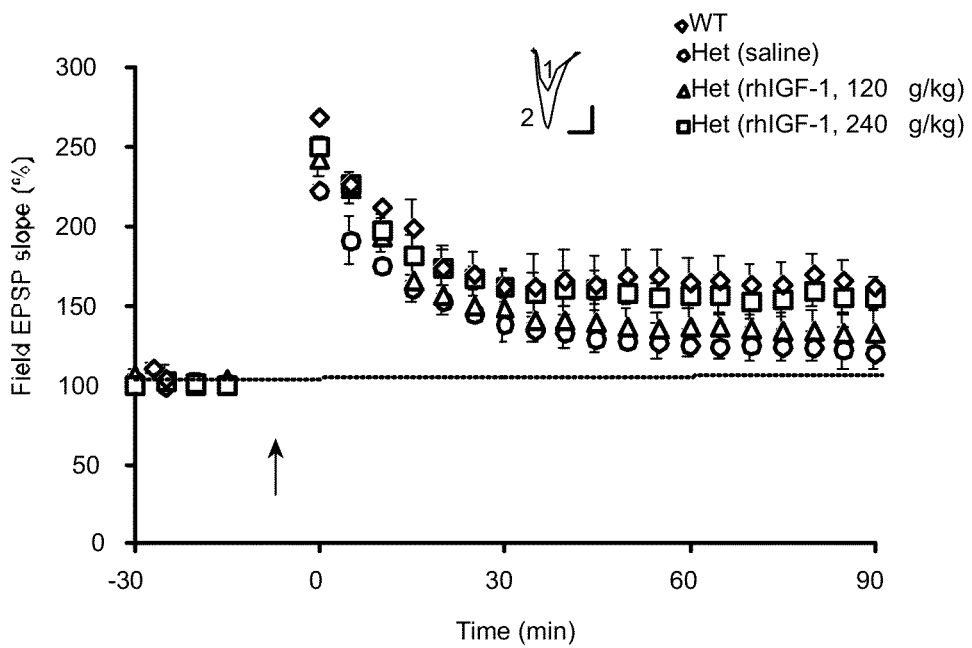
Figure 10B:
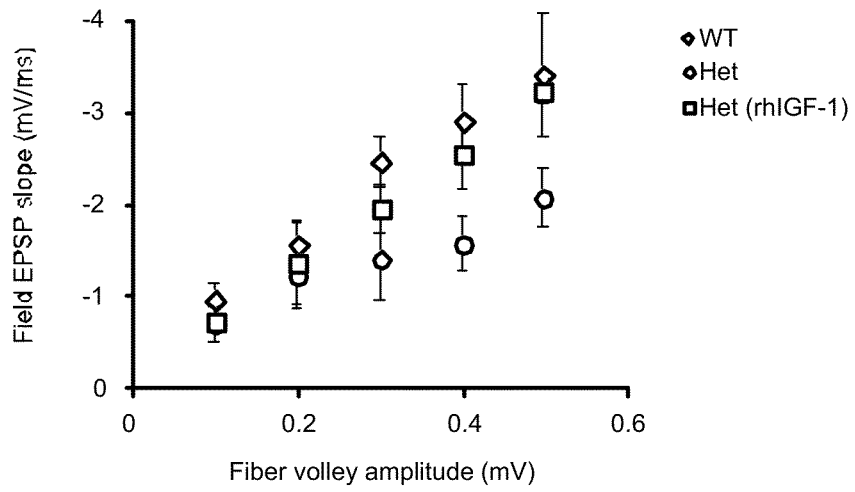

IGF-1 has been approved for clinical use as a recombinant full-length protein. Full-length IGF-1 enters the CNS through an interaction with lipoprotein-related receptor 1 (LRP1), after activity dependent cleavage of IGF binding protein-3 (IGFBP-3) by matrix metalloproteinase-9 (MMP9) (Nishijima et al., 2010). To investigate whether peripherally administered full-length IGF-1 could also reverse synaptic deficits, IGF-1 was administered by intraperitoneal injection at 240 μg/kg/day, starting at P13-15 and continuing for 2 weeks. This dose was chosen because it represents the maximum dose according to the current FDA label for IGF-1. This treatment was also effective in rescuing defective LTP in heterozygous mice (FIG. 10a). Furthermore, specific deficits in the AMPA receptor component of I/O function (Bozdagi et al., 2010) were reversed by this treatment (FIG. 10b). Mean slope of the I/O function was 0.625±0.08 for wildtype; 0.31±0.045 for Shank3 heterozygous and 0.618±0.075 for IGF-1 injected heterozygous mice (comparison between heterozygotes and IGF-1-injected heterozygotes, p=0.004). Importantly, lower dose IGF-1 (120 μg/kg/day for 2 weeks) was not associated with significant reversal of deficits in LTP (FIG. 10a), showing a dose-response effect and providing preclinical dosing information.

Phelan-McDermid syndrome frequently presents with hypotonia and at least transient motor deficits, and subtle motor deficits have been observed in Shank3-heterozygous mice (Bozdagi et al., 2010). To determine whether treatment with full-length IGF-1 may improve motor performance in Shank3-deficient mice, male heterozygous mice were treated with either vehicle or IGF-1 (240 μg/kg/day for 2 weeks). Significant enhancement of motor performance was observed following treatment (FIG. 11).

To date, pharmacological treatments for ASD and other neurodevelopmental disorders are primarily ameliorative, focusing on managing associated symptoms such as anxiety, aggression, repetitive behaviors, or epilepsy (King et al., 2006). Pharmacological treatments addressing "core" deficits, such as cognitive impairments, social deficits, and absent or delayed speech, do not yet exist. Recently, however, the field has begun to see the evaluation of therapies targeted to etiology ("personalized medicine")—each arising from the basic analysis of model systems—in neurodevelopmental disorders including Fragile X syndrome, tuberous sclerosis, and Rett syndrome (Bear et al., 2004; Ehninger et al., 2009; Tropea et al., 2009).

It is interesting to note that IGF-1 activates the mTOR/Akt pathway as this has been implicated in other neurodevelopmental disorders (Veenstra-Vanderweele et al., 2012). It was therefore predicted that phospho-Akt/Akt ratios would be increased after IGF-1 treatment, and this is what was observed in studies in hippocampal lysates (0.36±0.03 and 0.55±0.04 in Shank3 heterozygous mice injected for 2 weeks with vehicle [n=8] or full-length IGF-1 protein [n=10], respectively; 1-tailed p=0.040).

Loss of one functional copy of the SHANK3 gene, through either mutation or deletion, is found in about 0.5% of ASD (Abrahams and Geschwind, 2008) and in about 0.3% of the developmentally delayed population (Cooper et al., 2011). As such it represents one of the more frequent causes of these disorders and a significant health burden. In addition, there is emerging evidence that the SHANK3 pathway may play a role in other neurodevelopmental disorders, as evidenced by large-scale proteomic and gene expression studies (Darnell et al., 2011; Sakai et al., 2011). Even more broadly, deficits in proteins associated with the postsynaptic density, which is in no small degree sculpted by SHANK3 (Roussignol et al., 2005), are associated with neurodevelopmental disorders (Laumonnier et al., 2007). Mutations in SHANK3 are also associated with schizophrenia (Gauthier et al., 2010). This indicates that therapies for SHANK3 deficiency and synaptic development represent important targets that can have broad positive impact in neurodevelopmental disorders (Melom and Littleton, 2011). These results show that IGF-1, approved for use in children, can lead to functional improvements in a mouse model of ASD and developmental delay, representing an important preclinical step.

REFERENCES

Abrahams, B. S. & Geschwind, D. H. Advances in autism genetics: on the threshold of a new neurobiology. *Nature reviews. Genetics* 9, 341-355 (2008).

Bats C, Groc L, Choquet D. The interaction between Stargazin and PSD-95 regulates AMPA receptor surface trafficking Neuron. 2007 Mar. 1; 53(5):719-34.

Bangash M A, Park J M, Melnikova T, Wang D, Jeon S K, Lee D, Syeda S, Kim J, Kouser M, Schwartz J, Cui Y, Zhao X, Speed H E, Kee S E, Tu J C, Hu J H, Petralia R S, et al. Enhanced Polyubiquitination of Shank3 and NMDA Receptor in a Mouse Model of Autism. Cell. 2011 May 11. [Epub ahead of print].

Baron, Marisa K, Tobias M Boeckers, Bianca Vaida, Salem Faham, Mari Gingery, Michael R Sawaya, et al. 2006. An architectural framework that may lie at the core of the postsynaptic density. Science 311, no. 5760 (January 27): 531-5.

Bear, M. F., Huber, K. M. & Warren, S. T. The mGluR theory of fragile X mental retardation. *Trends Neurosci* 27, 370-377 (2004).

Beni, Silvana, Noemi Tonna, Giorgia Menozzi, Maria Clara Bonaglia, Carlo Sala, Roberto Giorda, et al. 2007. DNA methylation regulates tissue-specific expression of Shank3 Journal of Neurochemistry 101, no. 5 (June): 1380-91.

Boeckers, T M. 2006. The postsynaptic density. Cell and Tissue Research 326, no. 2 (November): 409-22.

Bonaglia, M C, R Giorda, R Borgatti, G Felisari, C Gagliardi, A Selicorni, et al. 2001. Disruption of the ProSAP2 gene in a t(12;22)(q24.1;q13.3) is associated with the 22q13.3 deletion syndrome. American Journal of Human Genetics 69 (2): 261-8.

Bonaglia, M C, R Giorda, E Mani, G Aceti, B-M Anderlid, A Baroncini, et al. 2006. Identification of a recurrent breakpoint within the SHANK3 gene in the 22q13.3 deletion syndrome. Journal of Medical Genetics 43, no. 10 (October): 822-8.

Bonaglia M C, et al. Molecular mechanisms generating and stabilizing terminal 22q13 deletions in 44 subjects with Phelan/McDermid syndrome. PLoS Genet. 2011 July; 7(7): e1002173. Epub 2011 Jul. 14.

Bozdagi O, Sakurai T, Papapetrou D, Wang X, Dickstein DL, Takahashi N, Kajiwara Y, Yang M, Katz A M, Scattoni M L, Harris M J, Saxena R, Silverman J L, Crawley J N, Zhou Q, Hof P R, Buxbaum J D. Haploinsufficiency of the autism-associated Shank3 gene leads to deficits in synaptic function, social interaction, and social communication. Mol Autism. 2010 Dec. 17; 1(1):15.

Brakeman P R, Lanahan A A, O'Brien R, Roche K, Barnes C A, Huganir R L, Worley P F. Homer: a protein that selectively binds metabotropic glutamate receptors. Nature. 1997 Mar. 20; 386(6622):284-8.

Ching, Tsui-Ting, Alika K Maunakea, Peter Jun, Chibo Hong, Giuseppe Zardo, Daniel Pinkel, et al. 2005. Epigenome analyses using BAC microarrays identify evolutionary conservation of tissue-specific methylation of SHANK3. Nature Genetics 37, no. 6 (June): 645-51.

Cooper, G. M. et al. A copy number variation morbidity map of developmental delay. *Nature genetics* 43, 838-846 (2011).

Darnell, J. C. et al. FMRP stalls ribosomal translocation on mRNAs linked to synaptic function and autism. *Cell* 146, 247-261 (2011).

Durand, Christelle M, Catalina Betancur, Tobias M Boeckers, Juergen Bockmann, Pauline Chaste, Fabien Fauchereau, et al. 2007. Mutations in the gene encoding the synaptic scaffolding protein SHANK3 are associated with autism spectrum disorders. Nature Genetics 39, no. 1 (January): 25-7.

Ehninger, D., de Vries, P. J. & Silva, A. J. From mTOR to cognition: molecular and cellular mechanisms of cognitive impairments in tuberous sclerosis. *J Intellect Disabil Res* 53, 838-851 (2009).

Farr, Carol D, Philip R Gafken, Angela D Norbeck, Catalin E Doneanu, Martha D Stapels, Douglas F Barofsky, et al. 2004. Proteomic analysis of native metabotropic glutamate receptor 5 protein complexes reveals novel molecular constituents. Journal of Neurochemistry 91, no. 2 (October): 438-50.

Gauthier J, Spiegelman D, Piton A, Lafreniere R G, Laurent S, St-Onge J, Lapointe L, Hamdan F F, Cossette P, Mottron L, Fombonne E, Joober R, Marineau C, Drapeau P, Rouleau G A. Novel de novo SHANK3 mutation in autistic patients. Am J Med Genet B Neuropsychiatr Genet. 2009 Apr. 5; 150B(3):421-4.

Gauthier J, Champagne N, Lafreniere R G, Xiong L, Spiegelman D, Brustein E, Lapointe M, Peng H, Cote M, Noreau A, Hamdan F F, Addington A M, Rapoport J L, et al. De novo mutations in the gene encoding the synaptic scaffolding protein SHANK3 in patients ascertained for schizophrenia. Proc Natl Acad Sci U S A. 2010 Apr. 27; 107(17): 7863-8. Epub 2010 Apr. 12.

Hamdan F F, Gauthier J, Araki Y, Lin D T, Yoshizawa Y, Higashi K, Park A R, Spiegelman D, Dobrzeniecka S, Piton A, Tomitori H, Daoud H, Massicotte C, Henrion E, et al. Excess of de novo deleterious mutations in genes associated with glutamatergic systems in nonsyndromic intellectual disability. Am J Hum Genet. 2011 Mar. 11;88(3):306-16. Epub 2011 Mar. 3.

Hering, Heike, and Morgan Sheng. 2003. Activity-dependent redistribution and essential role of cortactin in dendritic spine morphogenesis. J Neurosci 23 (37): 11759-69.

Hung A Y, Futai K, Sala C, Valtschanoff J G, Ryu J, Woodworth M A, Kidd F L, Sung C C, Miyakawa T, Bear M F, Weinberg R J, Sheng M. Smaller dendritic spines, weaker synaptic transmission, but enhanced spatial learning in mice lacking Shank1. J Neurosci 2008; 28(7): 1697-1708.

Husi, H, M A Ward, J S Choudhary, W P Blackstock, and S G Grant. 2000. Proteomic analysis of NMDA receptor-adhesion protein signaling complexes. Nature Neuroscience 3, no. 7 (July): 661-9.

King, B. H. & Bostic, J. Q. An update on pharmacologic treatments for autism spectrum disorders. *Child Adolesc Psychiatr Clin N Am* 15, 161-175, (2006).

Luciani J J, de Mas P, Depetris D, Mignon-Ravix C, Bottani A, Prieur M, Jonveaux P, Philippe A, Bourrouillou G, de Martinville B, Delobel B, Vallee L, Croquette M F, Mattei M G. Telomeric 22q13 deletions resulting from rings, simple deletions, and translocations: cytogenetic, molecular, and clinical analyses of 32 new observations. J Med Genet 2003; 40(9): 690-696.

Melom, J. E. & Littleton, J. T. Synapse development in health and disease. Current opinion in genetics & development 21, 256-261 (2011).

Moessner R, Marshall C R, Sutcliffe J S, Skaug J, Pinto D, Vincent J, Zwaigenbaum L, Fernandez B, Roberts W, Szatmari P, Scherer S W. Contribution of SHANK3 mutations to autism spectrum disorder. Am J Hum Genet 2007; 81(6): 1289-1297.

Naisbitt, S, E Kim, J C Tu, B Xiao, C Sala, J Valtschanoff, et al. 1999. Shank, a novel family of postsynaptic density proteins that binds to the NMDA receptor/PSD-95/GKAP complex and cortactin. Neuron 23, no. 3 (July): 569-82.

Nishijima, T. et al. Neuronal activity drives localized blood-brain-barrier transport of serum insulin-like growth factor-I into the CNS. *Neuron* 67, 834-846 (2010).

Okabe, Shigeo. 2007. Molecular anatomy of the postsynaptic density. Molecular and Cellular Neurosciences 34, no. 4 (April): 503-18.

O'Kusky, J. R., Ye, P. & D'Ercole, A. J. Insulin-like growth factor-I promotes neurogenesis and synaptogenesis in the hippocampal dentate gyrus during postnatal development. *The Journal of Neuroscience* 20, 8435-8442 (2000).

Peca J, Feliciano C, Ting J T, Wang W, Wells M F, Venkatraman T N, Lascola C D, Fu Z, Feng G. Shank3 mutant mice display autistic-like behaviours and striatal dysfunction. Nature. 2011 Apr. 28; 472(7344):437-42. Epub 2011 Mar. 20.

Phelan M C, Rogers R C, Saul R A, Stapleton G A, Sweet K, McDermid H, Shaw S R, Claytor J, Willis J, Kelly D P. 22q13 deletion syndrome. Am J Med Genet 2001; 101: 91-9.

Qiao, Feng, and James U Bowie. 2005. The many faces of SAM. Science's STKE : signal transduction knowledge environment 2005, no. 286 (May 31): re1.

Roussignol, Gautier, Fabrice Ango, Stefano Romorini, Jian Cheng Tu, Carlo Sala, Paul F Worley, et al. 2005. Shank expression is sufficient to induce functional dendritic spine synapses in aspiny neurons. Journal of Neuroscience 25(14) (April 6): 3560-70.

Sakai, Y. et al. Protein interactome reveals converging molecular pathways among autism disorders. *Science translational medicine* 3, 86ra49 (2011).

Sala, C, V Piech, N R Wilson, M Passafaro, G Liu, M Sheng, et al. 2001. Regulation of dendritic spine morphology and synaptic function by Shank and Homer. Neuron 31, no. 1 (July 19): 115-30.

Sala, Carlo, Gautier Roussignol, Jacopo Meldolesi, and Laurent Fagni. 2005. Key role of the postsynaptic density scaffold proteins Shank and Homer in the functional architecture of Ca2+ homeostasis at dendritic spines in hippocampal neurons. J Neurosci 25(18): 4587-92.

Sugiyama, Yoshiko, Izumi Kawabata, Kenji Sobue, and Shigeo Okabe. 2005. Determination of absolute protein numbers in single synapses by a GFP-based calibration technique. Nature Methods 2, no. 9 (September): 677-84.

Tropea, D. et al. Partial reversal of Rett Syndrome-like symptoms in MeCP2 mutant mice. *Proceedings of the National Academy of Sciences of the United States of America* 106, 2029-2034 (2009).

Tu J C, Xiao B, Naisbitt S, Yuan J P, Petralia R S, Brakeman P, Doan A, Aakalu V K, Lanahan A A, Sheng M, Worley P F. Coupling of mGluR/Homer and PSD-95 complexes by the Shank family of postsynaptic density proteins. Neuron 1999; 23(3): 583-592.

Uchino S, Wada H, Honda S, Nakamura Y, Ondo Y, Uchiyama T, Tsutsumi M, Suzuki E, Hirasawa T, Kohsaka S. Direct interaction of post-synaptic density-95/Dlg/ZO-1 domain-containing synaptic molecule Shank3 with GluR1 alpha-amino-3-hydroxy-5-methyl-4-isoxazole propionic acid receptor. J Neurochem 2006; 97(4): 1203-14.

Veenstra-Vanderweele, J. & Blakely, R. D. Networking in autism: leveraging genetic, biomarker and model system findings in the search for new treatments. *Neuropsychopharmacology* 37, 196-212 (2012).

Vorstman, J A S, W G Staal, E van Daalen, H van Engeland, P F R Hochstenbach, L Franke, et al. 2006. Identification of novel autism candidate regions through analysis of reported cytogenetic abnormalities associated with autism. Molecular Psychiatry 11, no. 1 (January): 1, 18-28.

Wang X, McCoy P, Rodriguiz R M, Pan Y, Je H S, Roberts A, Kim C, Berrios J, Colvin J S, Bousquet-Moore D, Lorenzo I, Wu G, Weinberg R J, Ehlers M D, Philpot B D, Beaudet A L, Wetsel W C, Jiang Y H. Synaptic dysfunction and abnormal behaviors in mice lacking major isoforms of Shank3 Hum Mol Genet. 2011 May 10.

Wilson H L, Wong A C, Shaw S R, Tse W Y, Stapleton G A, Phelan M C, Hu S, Marshall J, McDermid H E. Molecular characterisation of the 22q13 deletion syndrome supports the role of haploinsufficiency of SHANK3/PROSAP2 in the major neurological symptoms. J Med Genet. 2003 August; 40(8):575-84.

Wong, A C, Y Ning, J Flint, K Clark, J P Dumanski, D H Ledbetter, et al. 1997. Molecular characterization of a 130-kb terminal microdeletion at 22q in a child with mild mental retardation. American Journal of Human Genetics 60 (1): 113-20.

What is claimed is:

1. A method for treating a human subject with Phelan-McDermid Syndrome comprising administering insulin-like growth factor 1 (IGF-1) to the human subject in an amount and manner effective to alleviate a motor deficit.

* * * * *